United States Patent
Fernandes De Oliveira et al.

(10) Patent No.: US 11,623,862 B2
(45) Date of Patent: Apr. 11, 2023

(54) TRANSITION METAL CARBIDE CHEMICAL LOOPING REFORMING

(71) Applicant: UTI Limited Partnership, Calgary (CA)

(72) Inventors: Camilla Fernandes De Oliveira, Calgary (CA); Luis Daniel Virla Alvarado, Calgary (CA); Nader Mahinpey, Calgary (CA)

(73) Assignee: UTI LIMITED PARTNERSHIP, Calgary (CA)

(*) Notice: Subject to any disclaimer, the term of this patent is extended or adjusted under 35 U.S.C. 154(b) by 120 days.

(21) Appl. No.: 17/068,372

(22) Filed: Oct. 12, 2020

(65) Prior Publication Data

US 2021/0114871 A1    Apr. 22, 2021

Related U.S. Application Data

(60) Provisional application No. 62/916,389, filed on Oct. 17, 2019.

(51) Int. Cl.
| | |
|---|---|
| *C01B 3/34* | (2006.01) |
| *C01B 3/02* | (2006.01) |
| *C07C 29/151* | (2006.01) |
| *C07C 41/01* | (2006.01) |

(52) U.S. Cl.
CPC ............ *C01B 3/344* (2013.01); *C01B 3/025* (2013.01); *C07C 29/1518* (2013.01); *C07C 41/01* (2013.01); *C01B 2203/0255* (2013.01); *C01B 2203/061* (2013.01); *C01B 2203/062* (2013.01); *C01B 2203/068* (2013.01); *C01B 2203/1241* (2013.01)

(58) Field of Classification Search
CPC ... C01B 3/386; C01B 3/40; C01B 2203/0261; C01B 2203/1041; C01B 2203/1047; C01B 2203/1241; C01B 2203/80; B01J 23/24; B01J 27/22; B01J 37/084
See application file for complete search history.

(56) References Cited

U.S. PATENT DOCUMENTS

| | | | |
|---|---|---|---|
| 10,315,176 B2 | 6/2019 | Adham et al. | |
| 2002/0198101 A1* | 12/2002 | Gaffney | B01J 37/084 502/177 |

OTHER PUBLICATIONS

Claridge et al., synthesis of early transition metal carbides and their application for reforming of methane to synthesis gas, (PII S0167-2991 (97)81033-6 Elsevier Enhanced Reader).*
H. Khan and J. Paisie, Global Syngas Overview, slideshare.net, Oct. 31, 2019; https://www.slideshare.net/StratasAdvisors/stratas-advisors-global-syngas-overview-by-dr-habib-khan.
L.F Diego et al., Chem. Eng. J. 2008, 144, 289-298.

(Continued)

*Primary Examiner* — Jafar F Parsa

(74) *Attorney, Agent, or Firm* — Nguyen Tarbet LLC

(57) ABSTRACT

A process for producing syngas including at least $H_2$ and CO. The process includes the steps of a) generating a transition metal carbide by reacting a corresponding transition metal oxide with a fuel to produce a stream of syngas; and b) combining the transition metal carbide with oxygen to oxidize the transition metal carbide to regenerate the corresponding transition metal oxide, thereby producing a gas output comprising at least one or more oxidized carbon compounds and heat for autothermal operation.

20 Claims, 33 Drawing Sheets

(56) References Cited

OTHER PUBLICATIONS

Y. Cao et al., Energy & Fuels, 2008, 22, 1720-1730.
J. Adanez et al., Prog. Energy Combust. Sci., 2012, 38, 215-282.
M. Tang et al., Appl. Energy, 2015, 151, 143-156.
M. Voldsund et al., Int. J. Hydrogen Energy, 2016, 41, 4969-4992.
C. Ferguson et al., "Catalyst for Change—Which chemical companies are prepared for the low carbon transition?"—CDP UK Report, Oct. 2017.
J. Adanez et al., Prog. Energy Combust. Sci., 2018, 65, 6-66.
M. Najera et al., Chem. Eng. Res & Design, 2011, 89, 1533-1543.
L.D. Virla Alvaredo, University of Calgary Thesis, Apr. 30, 2018.
O. Ostrovski & G. Zhang, AIChE J. 2006, 52, 300-310.
G. Zhang & O. Ostrovski, Metallurg. Mat. Trans. B, 2000, 31B, 129-139.
S. C. Bayham et al., WIREs Energy Environ., 2016, 5, 216-241.
J. Adanez et al., Energy & Fuels, 2004, 18, 371-377.
S. T Oyama, The chemistry of transition metal carbides and nitrides, First Edition. Glasgow: Blackie Academic & Professional, 1996.
Y. Ma et al., Renewable Sustainable Energy Rev. 2017, 75, 1101-1129.
J. B. Claridge et al., J. Catal., 1998, 180, 85-100.
O. Knacke et al., Thermo-chemical properties of Inorganic Substances, 1991, (2nd ed.). Berlin, New York: Springer, selected pages between p. 68 to 2410.
A. P. E. York et al., "Synthesis of early Transition Metal carbides and their Application for the Reforming of Methane to Synthesis Gas," in 3rd World Congress on Oxidation Catalysis, 1997, pp. 711-720.
D. E. Giles et al., 2006, Fuel, 1729-1742.
National Energy Technology Laboratory, "Range of Syngas Composition Across Different Gasifier Type, and Feedstock Produced by the Gasification of Coal Feedstocks." Accessed: Jul. 22, 2019. [Online]. Available: https://www.netl.doe.gov/sites/default/files/netl-file/Range-of-syngas-Comp.pdf.
J. P. Cifnero & J. J. Marano, U.S. Department of Energy National Energy Technology Laboratory "Benchmarking Biomass Gasification Technologies for Fuels, Chemicals and Hydrogen Production".
D. C. Lamont & W. J. Thomson, Chem. Eng. Sci., 2005, 60, 3553-3559.
D. Hunyadi et al., 2013, J. Thermal Anal. Calorimetry, 2014, 116, 329-337.
G. Collodi & F. Wheeler, Chem Eng. Transactions, 2010, 19, 37-42.
H.F. Abbas & W. M. A. Wan Daud, Int. J. Hydrogen Energy, 2010, 35, 1160-1190.
P. Roohi et al., Int. J. Mineral, Metallurgy Materials, 2016, 23, 339-347.
S. P. Garg et al., J. Phase Equilibria, 1996, 17, 63-77.
J. Dang et al., J. Alloys Compounds, 2018, 745, 421-429.
https://www.factsage.com/fs_pd.php, archived Sep. 16, 2017.
H. Okamoto, J. Phase Equilibria, 1992, 13, 543-565.
C. Fernandes de Oliveira, "Chemical Looping Reforming Using Transition Metal Carbides," University of Calgary, 2020.
J.-M. Giraudon et al., J. Solid State Chem. 2000, 154, 412-426.
Zheng et al., Chemical looping reforming: process fundamentals and oxygen carriers, Discover Chemical Engineering, 2022, 2:5 (https://doi.org/10.1007/s43938-022-00012-3), published online Jul. 25, 2022.

\* cited by examiner

TRANSITION METAL CARBIDE CHEMICAL LOOPING REFORMING

CROSS-REFERENCE TO RELATED APPLICATIONS

This application claims priority from U.S. Provisional Application Ser. No. 62/916,389, filed on Oct. 17, 2019, the entire disclosure of which is incorporated herein by reference.

FIELD

The invention relates to production of syngas ($H_2$, CO and $CO_2$) using a chemical looping process and more particularly to a syngas production process which uses cycling of transition metal carbides to provide a solution to energy demand, carbon emissions and other challenges.

BACKGROUND

Syngas, which is generally known as a mixture of gases predominately including hydrogen, carbon monoxide, and carbon dioxide, represents an essential input for the global chemical industry. It is estimated that 75% of the syngas produced globally is applied to chemical production (fertilizers, methanol, dimethyl ether and other industrial chemicals). The other portion is distributed between gaseous fuel, liquid fuel, and power production [1]. In 2014, 116,600.00 MWth of syngas was produced globally and growth of its production is expected to reach 213,100.00 MWth by 2020. Additionally, projections to 2024 indicate growth in syngas use by about 3% in the chemical industry, by about 16% in production of gaseous fuels, by about 9% in production of liquid fuels and by about 5% in power generation. The growth is expected to be mainly due to low oil prices. Moreover, individual syngas projects relating to production of liquid fuels and fertilizers have an estimated value of about $24 billion (USD). Other syngas production projects have a combined value of $43 billion (USD) [1].

The main challenges of producing syngas are related to carbon emissions and energy consumption. Research has continuously shown that steam reforming is very energy intensive and not flexible in terms of the quality of syngas produced with reference to the $H_2$/CO ratio [3]-[7]. As the need to access renewable energy sources increases, new processes for producing syngas in under less energy intensive conditions and with product flexibility is very important for the chemical industry. It is estimated that the chemical industry itself contributes to ⅛ of the global industrial emissions [8]. Therefore, it is also essential to reduce carbon intensity in chemical processes to meet the UN sustainable development goals and limit global temperature change to within 1.5° C. above those of pre-industrial levels.

SUMMARY

In accordance with one embodiment, there is provided a process for producing syngas including at least $H_2$ and CO. The process includes the steps of: a) generating a transition metal carbide by reacting a corresponding transition metal oxide with a fuel to produce a stream of syngas; and b) combining the transition metal carbide with oxygen to oxidize the transition metal carbide to regenerate the corresponding transition metal oxide, thereby producing a gas output comprising at least one or more oxidized carbon compounds. The process may further include cycling between steps a) and b).

The oxygen may be provided in a mixture of gases. In some embodiments, the mixture of gases is air.

In some embodiments, step a) is performed in a first reactor, step b) is performed in a second reactor, the transition metal carbide is transferred to the second reactor prior to step b) and the corresponding transition metal oxide is transferred back to the first reactor before cycling to step a).

In other embodiments, the transition metal is fixed in the two reactors while the gas composition is switched from a reducing gas mixture to an oxidizing gas mixture, with an inert purging prior to the switching step thereby generating the oxidized carbon compounds without moving the transition metal.

The process may further include routing at least a portion of the gas output of the second reactor to mix with the fuel prior to providing the fuel to the first reactor.

In some embodiments, the transition metal of the transition metal carbide and the corresponding transition metal oxide belongs to the groups IB to VIIIB of the periodic table of the elements. In some embodiments, the transition metal includes Mo, W, Mn, or Zr. In other embodiments, the transition metal of the transition metal carbide and the corresponding transition metal oxide includes Mo or W. In some embodiments, the transition metal of the transition metal carbide and the corresponding transition metal oxide includes Mo, and the process is initiated using heptamolybdate tetrahydrate. In other embodiments, the transition metal of the transition metal carbide and the corresponding transition metal oxide is W and the process is initiated using ammonium metatungstate hydrate.

In some embodiments, the temperature in the first reactor is between about 525° C. to about 1125° C. In other embodiments, the temperature in the first reactor is between about 525° C. to about 1025° C.

The fuel used in the process is a carbon source and may include $CH_4$, a $C_1$ to $C_4$ hydrocarbons, a fossil fuel mixture, biomass or coal.

In some embodiments, heat generated in the second reactor is used to provide heat to the first reactor. In some embodiments, excess heat generated in the second reactor which is not provided to the first reactor is used in a separate process for heat recovery. In some embodiments, the separate process is steam generation.

In some embodiments, when the stream of syngas has a ratio of $H_2$/CO exceeding about 3, the syngas is used for production of $H_2$ in a separate process. In other embodiments, when the stream of syngas has a ratio of $H_2$/CO below about 3, the syngas is used in a separate Fischer-Tropsch process, methanol production process or dimethyl ether production process.

In some embodiments, $CO_2$ is mixed with the fuel in step a).

In some embodiments, nitrogen is mixed with the fuel in step a) to produce nitrogen compounds for production of fertilizer or ammonia.

In some embodiments, the fuel includes greater than about 30% $CH_4$.

BRIEF DESCRIPTION OF THE DRAWINGS

Various objects, features and advantages of the invention will be apparent from the following description of particular embodiments of the invention, as illustrated in the accompanying drawings.

FIG. 18($b$) is a gas composition plot of mol ratio of gas vs. ($nCH_4/nCH_4+n$(metal oxide)) generated by the fuel reactor for metal oxides of molybdenum at 875° C.

FIG. 18($c$) is a gas composition plot of mol ratio of gas vs. ($nCH_4/nCH_4+n$(metal oxide)) generated by the fuel reactor for metal oxides of tungsten at 675° C.

FIG. 18($d$) is a gas composition plot of mol ratio of gas vs. ($nCH_4/nCH_4+n$(metal oxide)) generated by the fuel reactor for metal oxides of tungsten at 875° C.

FIG. 21($b$) is another embodiment of transition metal carbide chemical looping reforming (CCLR) with fuel reactor input of $CH_4$ and a stream of output gases from the air reactor being sent into the fuel reactor with the input of $CH_4$.

FIG. 22($b$) includes molar fraction stability fields for oxidation states of tungsten in the fuel reactor fed with $CH_4$ and the output of the air reactor.

FIG. 23($b$) shows molar fraction profile for gas products in the fuel reactor at 1148 K (875° C.), fed with $CH_4$ and the output of the air reactor.

FIG. 24($b$) is a plot of tungsten composition cycling between $WO_3$ and WC during CLLR.

FIG. 24($c$) includes XRD plots of air reactor samples.

FIG. 24($d$) includes XRD plots of fuel reactor samples.

DETAILED DESCRIPTION

Introduction and Rationale

Figure 1:
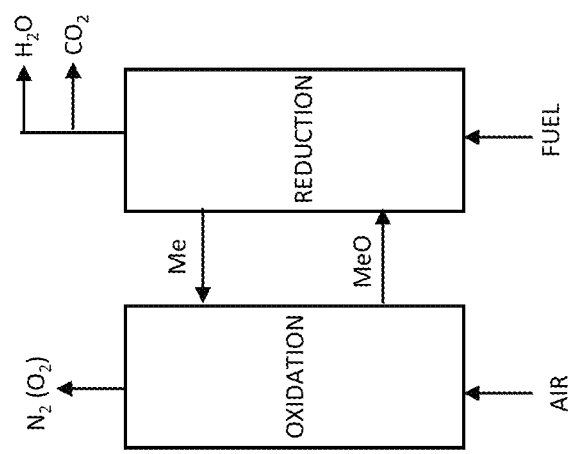
FIG. 1 is a schematic representation of a conventional chemical looping combustion process (CLC).

The inventive transition metal carbide chemical looping reforming process described herein (abbreviated as CLLR) has been developed as an improved variation related to processes known as chemical looping combustion and chemical looping reforming. FIG. 1 provides a schematic representation of chemical looping combustion (CLC), wherein a transition metal is oxidized in the presence of air in a first reactor and the oxidized transition metal is transferred to a second reactor to provide the oxidized transition metal as a source of oxygen for combustion. This removes the presence of $N_2$ in the second reactor and prevents formation of $NO_x$ species. The regenerated transition metal is transferred back to the first reactor creating a chemical loop wherein the process is cycled.

Figure 2:
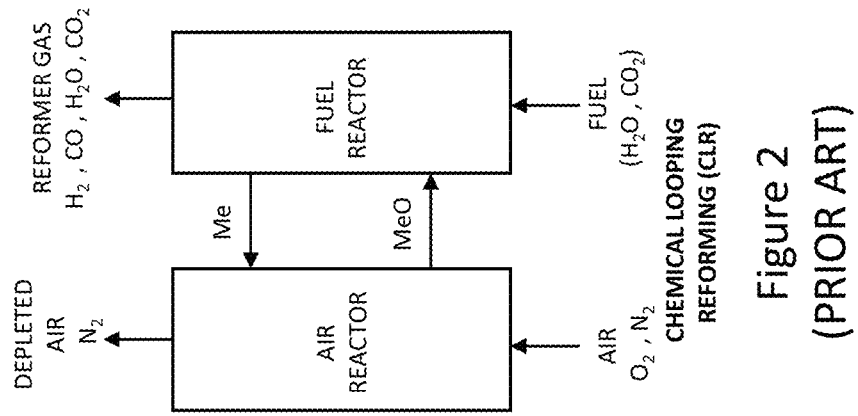
FIG. 2 is a schematic representation of a conventional chemical looping reforming process (CLR).

FIG. 2 provides a schematic representation of chemical looping reforming (CLR) where syngas (reformer gas) is produced in a fuel reactor after a transition metal is oxidized in an air reactor followed by transfer of the oxidized transition metal to the fuel reactor which is configured for production of syngas (reformer gas) using the oxidized transition metal as a source of oxygen for the reaction to produce the syngas.

Figure 3:
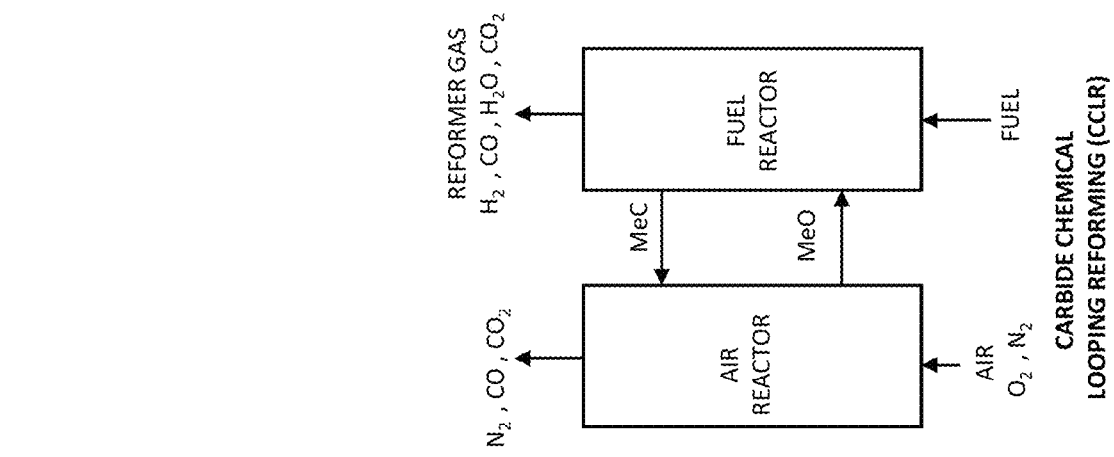
FIG. 3 is a schematic representation of an embodiment herein described as transition metal carbide chemical looping reforming.

FIG. 3 provides a schematic representation of the inventive process which is herein referred to as transition metal carbide chemical looping reforming (or carbide chemical looping reforming (CCLR)). This process is distinguished from CLC and CLR in in the fuel reactor, where the transition metal oxide is reduced to a carbide form instead to its metallic form with production of syngas having a high quantity of $H_2$. The oxidation of carbide in the air reactor is an exothermic reaction and produces sufficient energy to supply the process demand and produces extra energy that can be applied to other areas such as generation of steam or electricity [9]-[11].

CCLR is expected to provide an exceptional solution to energy demand, emissions and flexibility challenges. This process includes reduction of the metal oxide to carbide producing syngas with subsequent regeneration of the oxide through carbide oxidation with air. Calculations predict that this process can be run as low as about 575° C. Additionally, the syngas quality produced by this process can be provided with altered compositions upon changing the operational conditions and the transition metal used, with $H_2$/CO varying between about 1 to about 16. This flexibility provides the possibility to supply syngas to a wide range of applications such as the Fischer-Tropsch process, methanol and dimethyl ether production, and hydrogen production, among others.

The inventive process runs at high temperatures between about 575° C. to about 1025° C. and usually is carried out in fluidized bed reactor [12]. Due to its operating conditions, sintering [6] and attrition [13] may develop and impact the process performance. Carbides are well known for mechanical strength and high melting points [14]. These characteristics can address the aforementioned problems, making carbides promising materials for chemical looping reforming processes. An additional advantage is that carbide is also a catalyst for dry reforming reactions [15], [16], which can improve the achievement of high conversion of methane into syngas [6], [7], [12], [13], [15].

The inventive CCLR process described herein is expected to make a major contribution to the field of methane decarbonization and chemical synthesis by demonstrating the possibility of producing syngas without the need of external steam/$CO_2$ and heat.

Different transition metals from the groups IB to VIIIB of the periodic table of elements, such as Ti, Zr, Ta, Mo, W, Mn, Fe, Ni, V, were assessed for use in the CCLR process using the Gibbs minimization method to predict the composition of the solid and gas phase at equilibrium conditions and atmospheric pressure. Thermogravimetric analysis (TGA-MS) and X-ray diffraction (XRD) were used to confirm the thermodynamic estimations. The results indicate that the use of transition metals is limited by the carburization/oxidation efficiency and the melting point of the different metal species (oxides and carbides). Among different transition metals studied, tungsten (W) is the most promising option. Molybdenum (Mo) and zirconium (Zr) also have useful characteristics. Results using tungsten indicate syngas production between 575° C. to about 1025° C. and high oxide stability. In addition, oxidation of the tungsten carbide (WC), generates more heat than the heat required to generate WC, making the CCLR process autothermal.

Thermodynamic Modelling and Evaluation

A model of the CCLR process was evaluated at equilibrium to assess its feasibility under ideal conditions. It is common to evaluate new processes at equilibrium conditions before any experimental study, because the results represent the most likely conditions that allows the process to take place. Spontaneous processes tend to reach equilibrium when Gibbs energy is at its minimum. Following this logic, a Gibbs minimization model was developed on MATLAB (vR2018b) based on the work of Knacke, Kubaschewski and Hesselman including analytical thermochemical functions and thermochemical properties provided in *Thermochemical Properties of Inorganic Substances* [17]. The model was developed by Virla [9] and adapted to the reforming conditions used in this research. The assumptions of the model were that the gaseous products and reactants of the redox cycles would behave as ideal gases and its solids products and reactants that the partial Gibbs free energies of the reactants are the same as the standard Gibbs free energy. The constraints of the minimization algorithm were non-negativity and atomic balance between the different species in the solid and gas phase.

The thermodynamic study was applied to nine different transition metals, Ti, Zr, Ta, Mo, W, Mn, Fe, Ni, and V. The pressure was assumed to be constant at 1 atm. Temperature was varied from 298 K up to 1748 K in 50 K steps. The composition was varied with respect to the fuel reactor, the air reactor feed and the transition metal species. The carbides, oxides and nitride species of each transition metal were considered in this study. Additionally, the formation of C (graphite) was also considered. In the gas phase, the possible products considered were $CH_4$, $O_2$, $H_2$, CO, $CO_2$, $H_2O$, $NO_x$ and $N_2$. In this first screening, $CH_4$ was used as reducing agent and $O_2$ as oxidant agent. The data obtained in MATLAB was further treated in Excel and the figures were generated using OriginLab graphing software. The model was verified by replicating the estimations using FactSage®.

Materials

The metal precursor used for Mo was ammonium heptamolybdate tetrahydrate $((NH_4)_6Mo_7O_{24}.4H_2O)$ obtained from Sigma Aldrich with 81% purity (CAS: 12054-85-2). The metal precursor of W was ammonium metatungstate hydrate $((NH_4)_6H_2W_{12}O_{40}.H_2O)$ obtained from Sigma Aldrich with 85% purity (CAS: 12333-11-8). The metal precursors were used in the experiments without any kind of pre-treatment. The gases used in the measurements ($CH_4$, air and $N_2$) were obtained from Air Liquide with 99.99% purity.

Chemical Looping Reforming

The chemical looping reforming process was monitored using a thermogravimetric analyzer (TGA-MS) coupled with a Quadrupole Mass Spectrometer from MKS Cirrus-2 where the weight change of the oxygen carrier and outlet gas composition were monitored at different reaction conditions. This analysis enables the mass balance calculations to be made with respect to the formation of the different metal species. The weight changes in the solid phase should represent the transition of oxides into carbides and vice-versa within cycles of the reforming process. The conditions of the fuel reactor and the air reactor were simulated in NETZSCH TG 209 F1 Libra TGA in the EERG Laboratory at the University of Calgary. This apparatus is designed to measure weight in a controlled environment with respect to time and/or temperature changes. It is equipped with 1 inert line ($N_2$) and 2 purge lines that were used for the reactive gases ($CH_4$ and air). Its temperature range is between room temperature to 1100° C. and its weighting precision is 0.1 µg.

The experiments were conducted in redox cycles and at atmospheric pressure in Calgary (AB), Canada. An alumina crucible with a diameter of 6.8 mm, a volume of 85 µL was filled with 40 mg of metal precursor for the measurements. The fuel reactor conditions were replicated by a mixture of $CH_4$ and of $N_2$ at different concentrations. $N_2$ must be present in all the reactions because it protects the internal system and will always be part of the feeding mixture. The air reactor conditions were replicated by 10 mL/min of air (79% $N_2$ and 21% $O_2$) and 10 mL/min of $N_2$. The samples were heated from room temperature up to the desired temperature at a heating rate of 1 K/min. To prevent mixing of the methane generated by the reduction and oxygen from the oxidation in the furnace of the TGA, $N_2$ at 20 mL/min was purged for 6 min, before and after each cycle.

Product Characterization

Characterization of solid products was performed using a Rigaku Multiflex X-ray diffraction apparatus. Cu K-α was used as the radiation source and was operated at 40 kV and 40 mA. The measurements were obtained in 2θ from 10° to 90° at 1°/min and 0.02 step. This characterization method provides identification of unknown materials in the crystalline phase. Comparing standards (PFDs) to the obtained results, it is possible to identify the different species present in the sample. This characterization provides verification of formation of the species (oxide/carbide) predicted by the mass changes determined from the TGA.

Characterization of gases effluent was performed by a Micro-GC from Agilent Technologies model 490 and a quadrupole mass spectrometer from MKS model Cirrus 2. Both devices were baked prior to use and calibrated for the measurement of syngas products. The measurements enabled the verification of gas phase products and composition.

Results and Discussion

Figure 4:
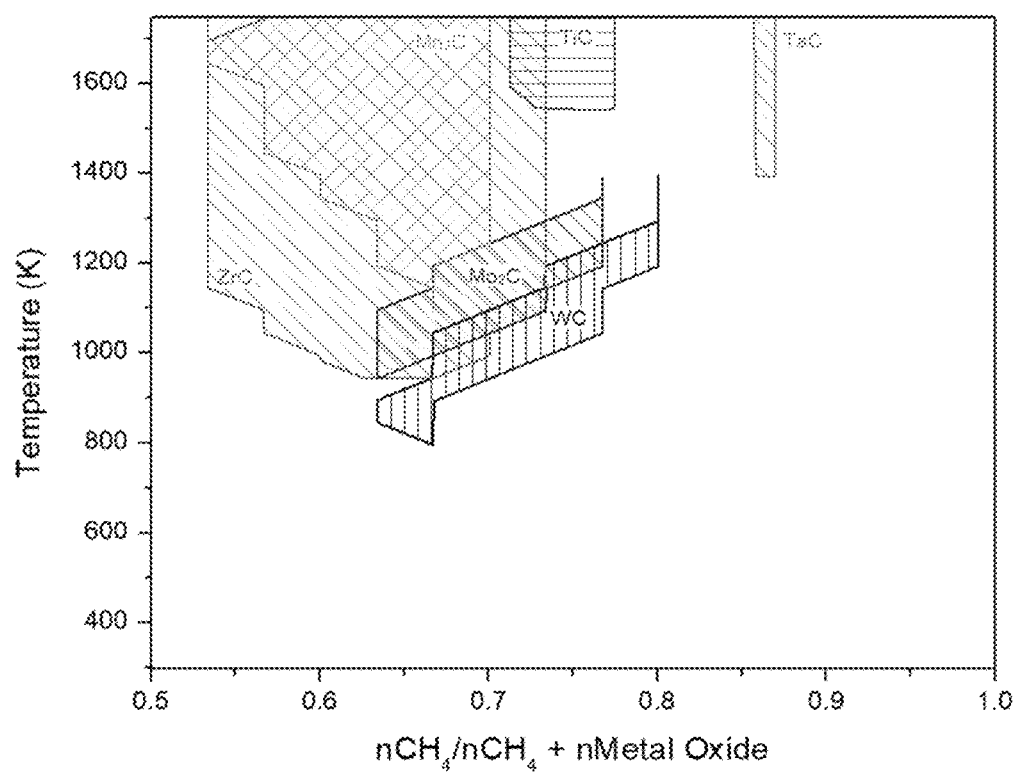
FIG. 4 is a diagram indicating suitable conditions for carbide formation for different transition metals.

Fuel Reactor-Syngas/$H_2$ Production—A phase equilibrium diagram of the different solid species studied was developed with the thermodynamic data. It was assumed that 1 mol of the most common oxide species is fed into the fuel reactor while the molar amount of $CH_4$ is varied. For the air reactor it was assumed that 1 mol of the most stable phase of the carbide species is fed while the molar amount of air is varied. FIG. 4 is a summary diagram indicating conditions where the carbide formation is favorable for different species and where the carbide is the only species in the solid phase. This diagram was prepared from selected regions from phase diagrams provided in FIGS. 5 to 17.

Figure 5:
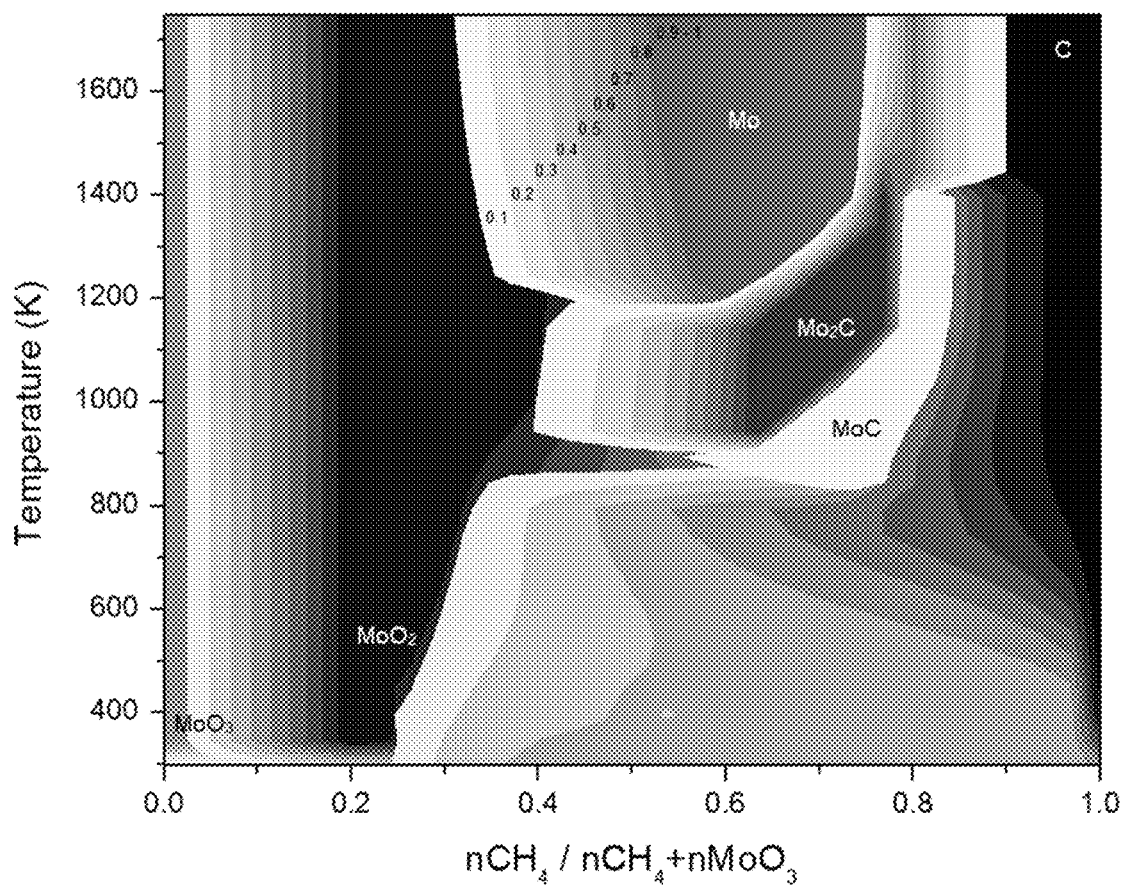
FIG. 5 is a phase diagram for solid species of molybdenum in the fuel reactor.

In FIG. 5 the different species formed during the reduction of $MoO_3$ using $CH_4$ under different conditions can be seen. The labelling of the different shades represents the different species and the spectrum in each shade represents the concentration of the species at given regions. For instance, in FIG. 5, at 0.1 of $CH_4$ ratio in the feed at 1200K the solid phase composition is 0.1 Mo and 0.9 $MoO_2$. This phase diagram simulates conditions in the fuel reactor where the carbide formation will be favored. The reduction of $MoO_3$ to $MoO_2$ is verified at low concentrations of $CH_4$. Therefore, to obtain carbides $MoO_3$ is fully converted to $MoO_2$. Consequently, the region where $Mo_2C$ is the only species in the solid phase is selected as the optimal region, which most likely to indicate an optimal operation condition ($CH_4$ ratio=0.627-0.759 and temperatures=675° C.-1125° C.). This result matches the findings of Virla [9]. In the case of molybdenum, two different species of carbides can be formed however $Mo_2C$ is known as the most stable molybdenum carbide phase. Consequently, in this study $Mo_2C$ is the carbide chosen to be potentially converted.

Figure 6:
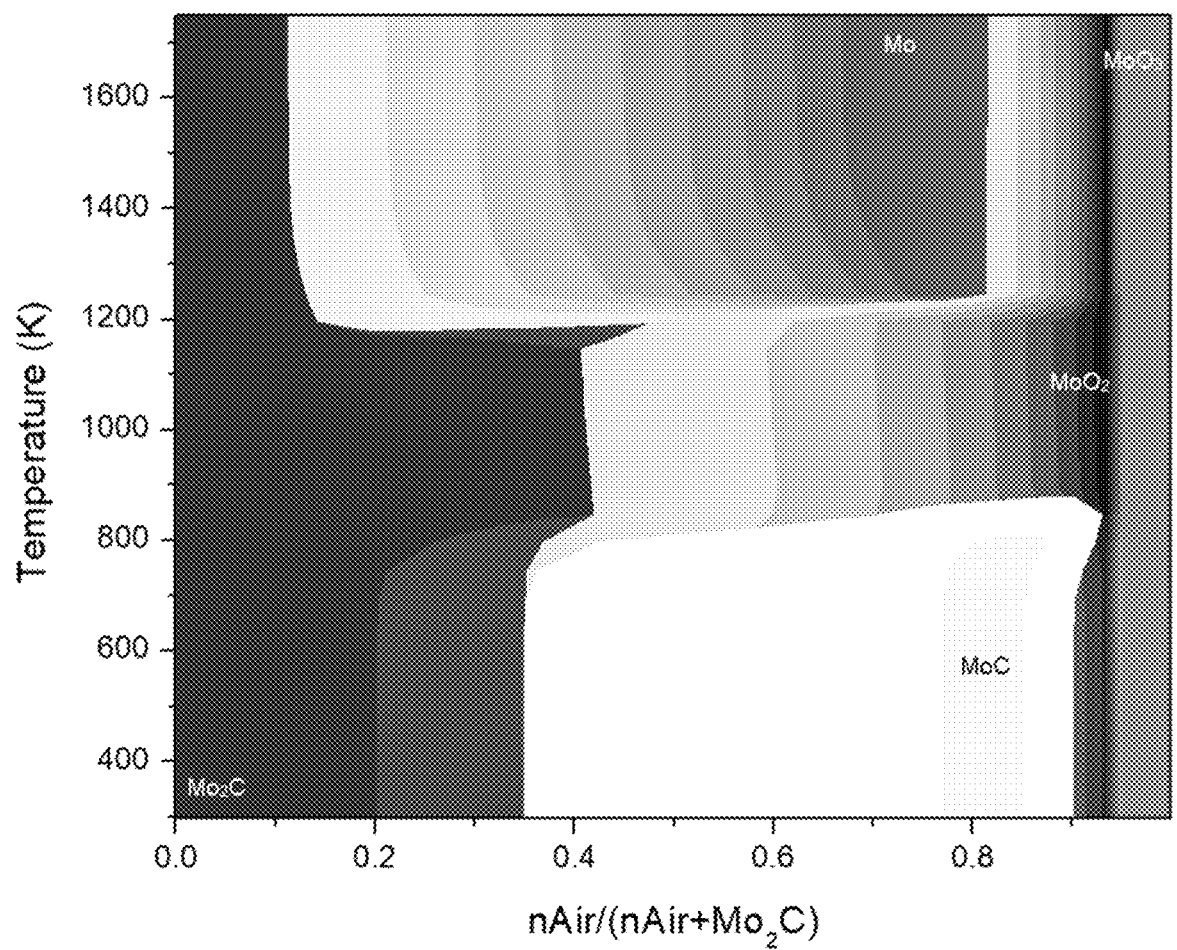
FIG. 6 is a phase diagram for solid species of molybdenum in the air reactor.
Figure 7:
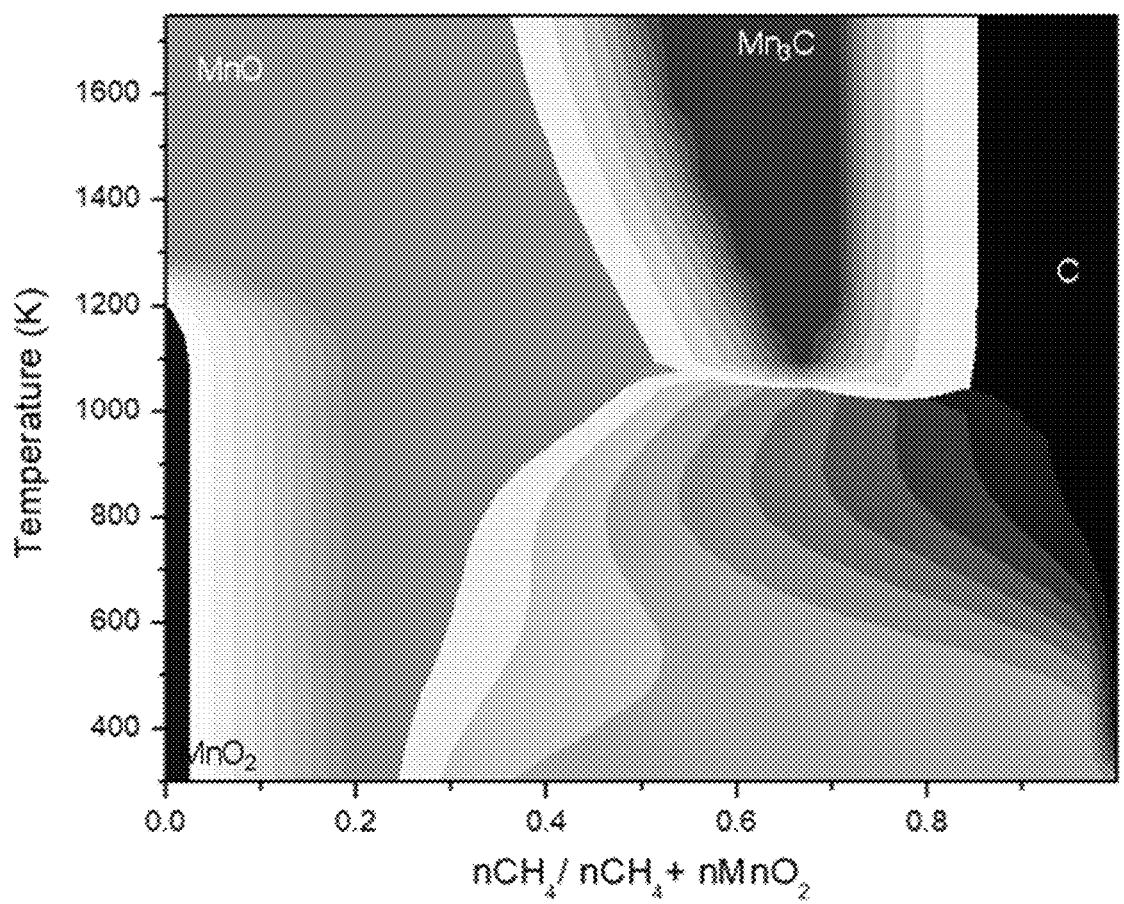
FIG. 7 is a phase diagram for solid species of manganese in the fuel reactor.
Figure 8:
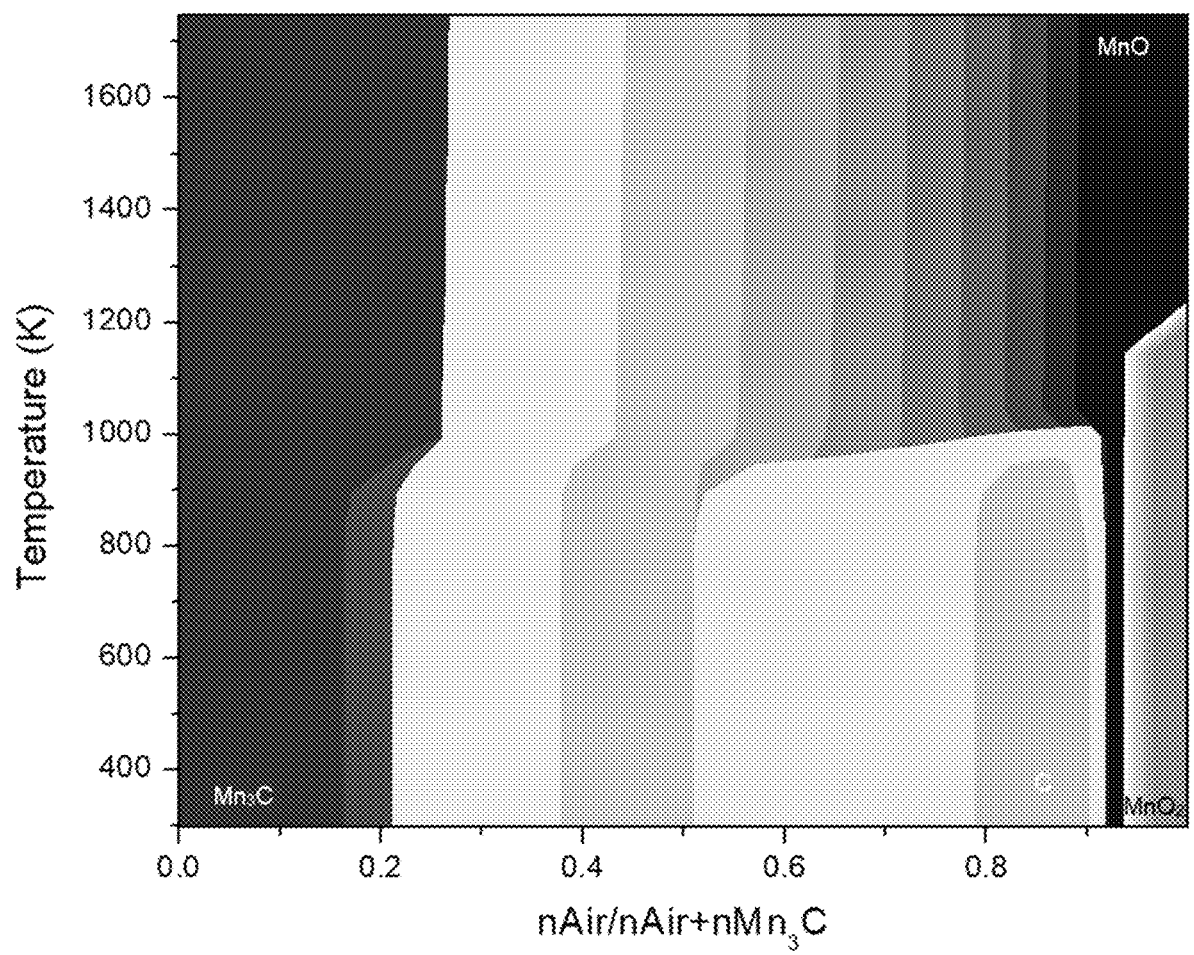
FIG. 8 is a phase diagram for solid species of manganese in the air reactor.
Figure 9:
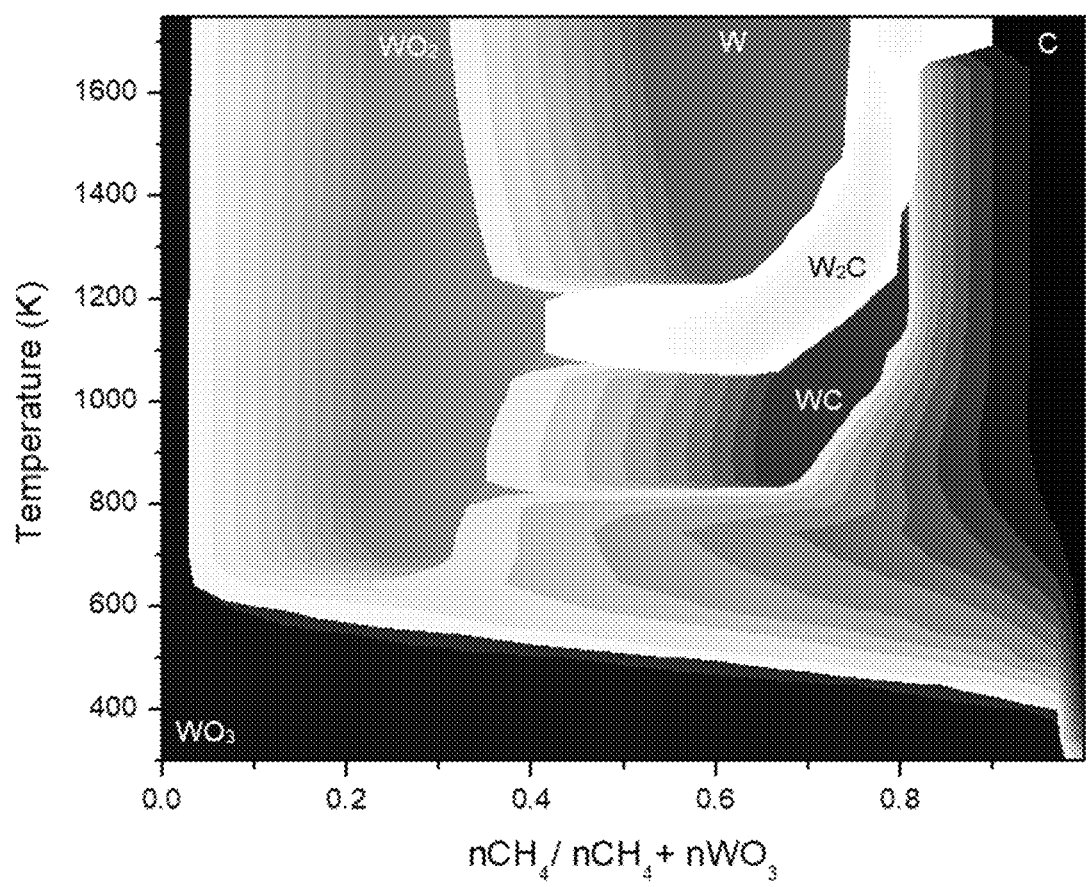
FIG. 9 is a phase diagram for solid species of tungsten in the fuel reactor.
Figure 10:
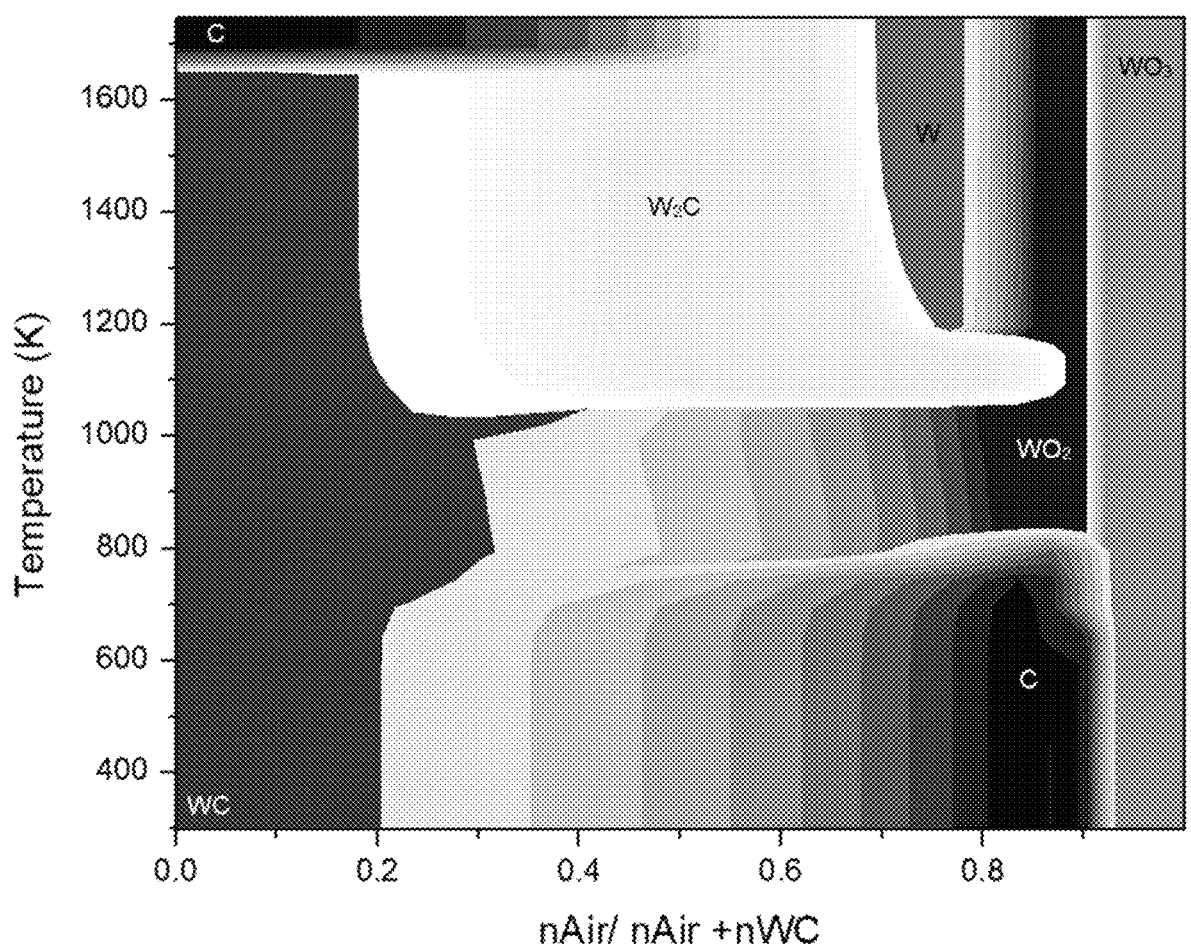
FIG. 10 is a phase diagram for solid species of tungsten in the air reactor.
Figure 11:
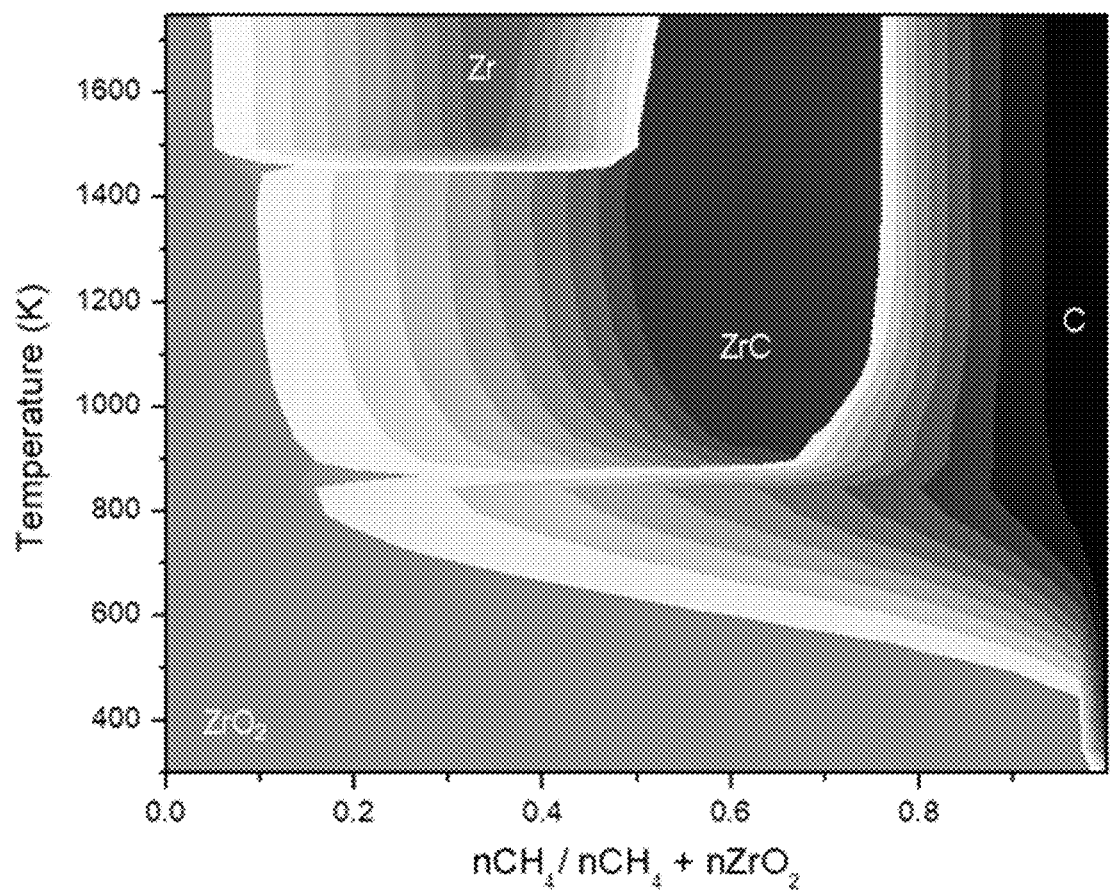
FIG. 11 is a phase diagram for solid species of zirconium in the fuel reactor.
Figure 12:
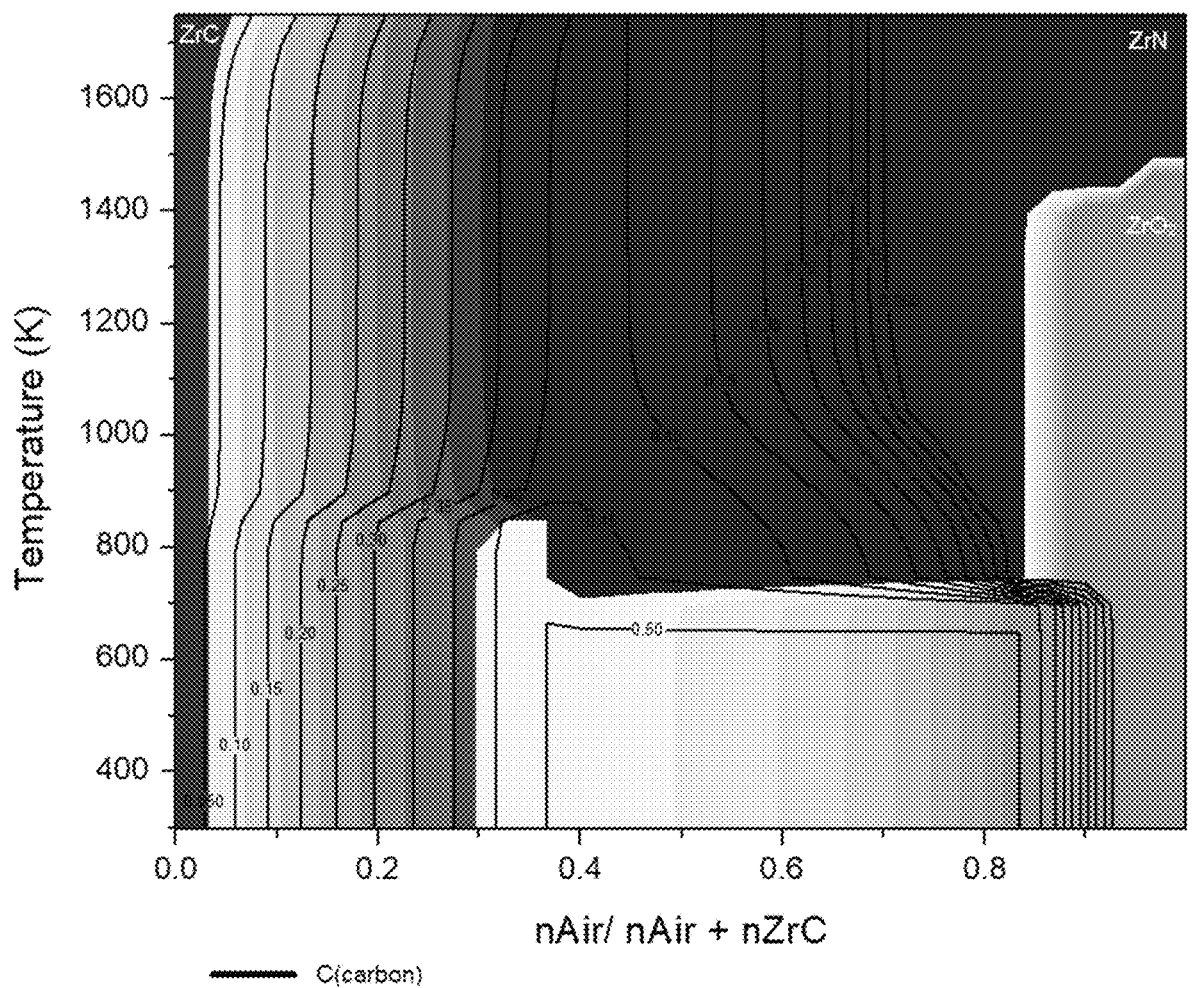
FIG. 12 is a phase diagram for solid species of zirconium in the air reactor.
Figure 13:
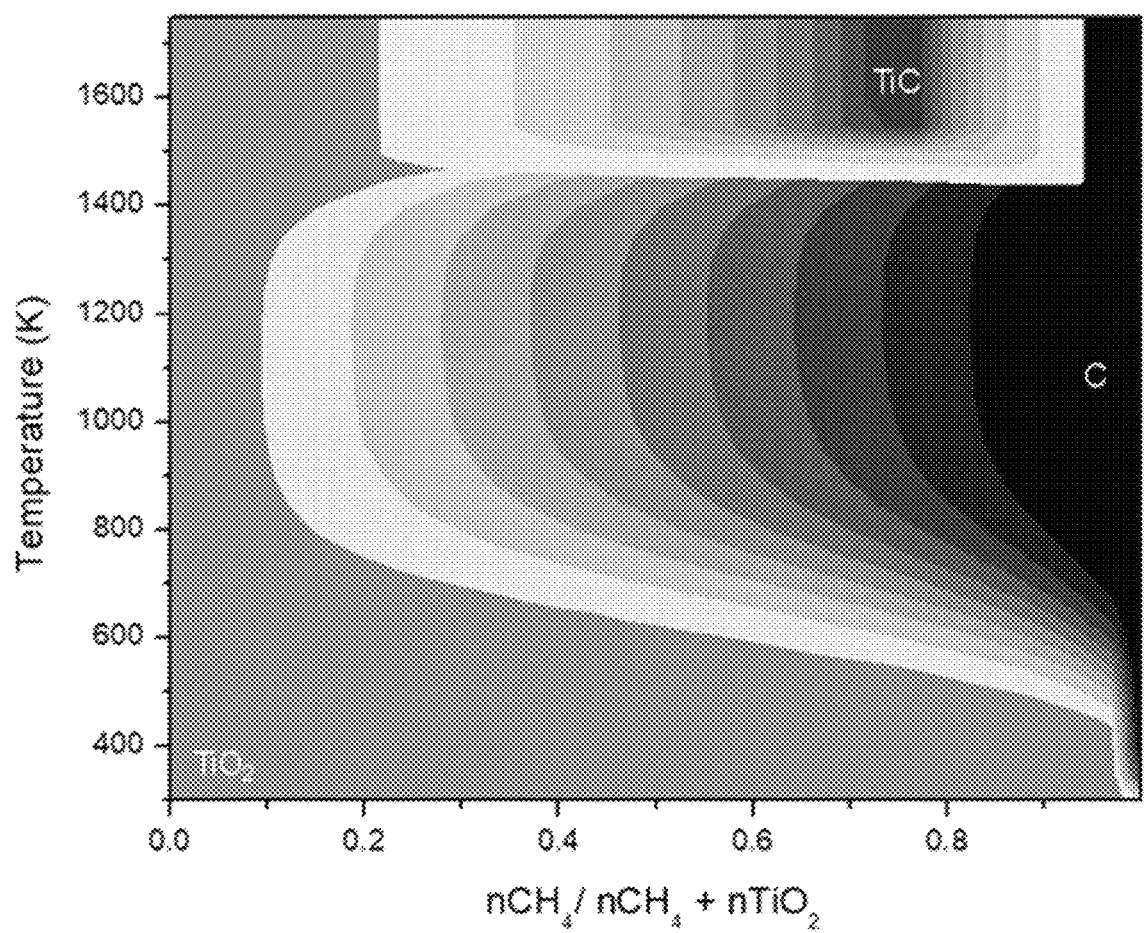
FIG. 13 is a phase diagram for solid species of titanium in the fuel reactor.
Figure 14:
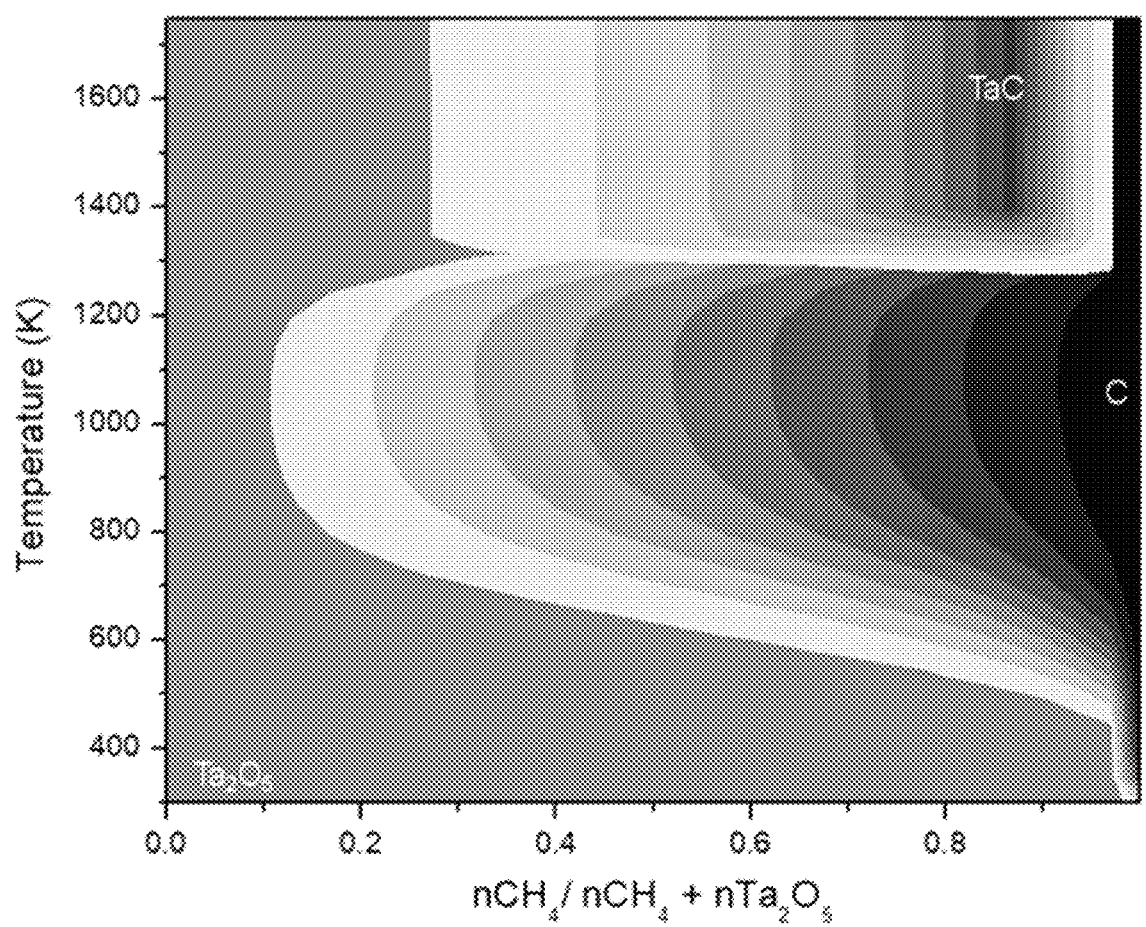
FIG. 14 is a phase diagram for solid species of tantalum in the fuel reactor.
Figure 15:
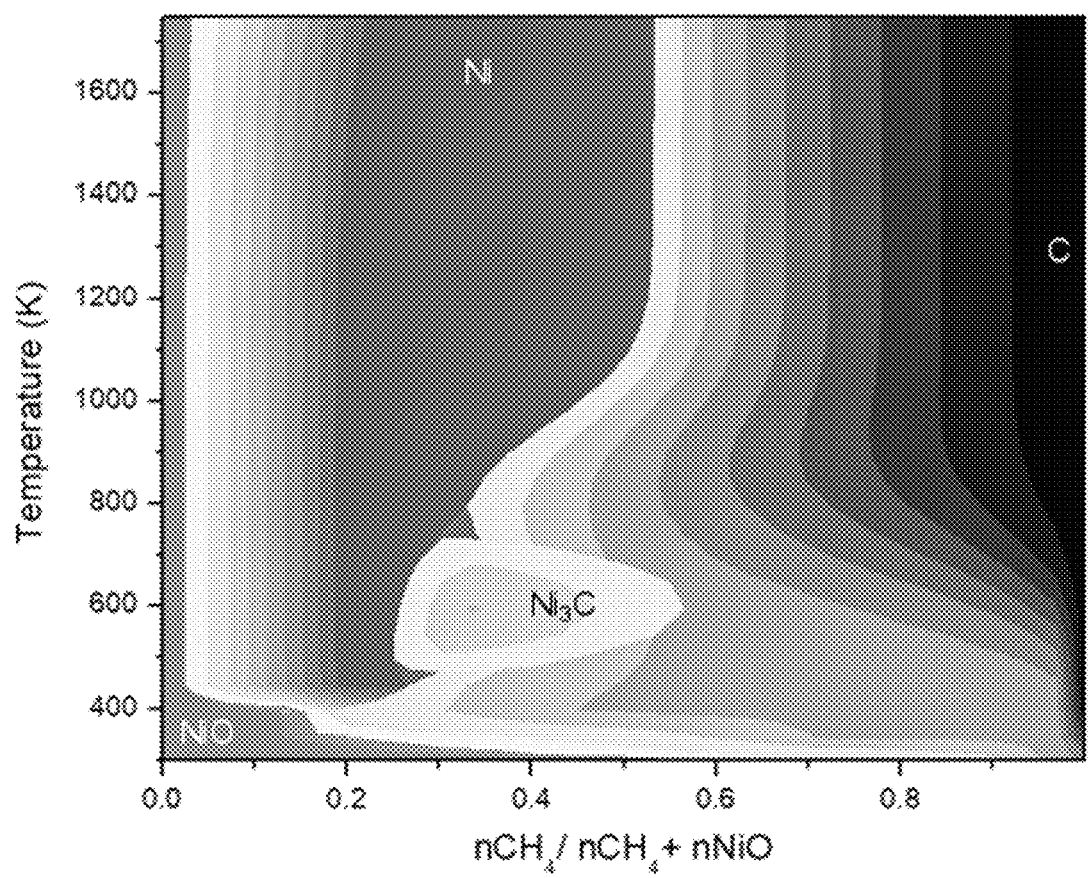
FIG. 15 is a phase diagram for solid species of nickel in the fuel reactor.
Figure 16:
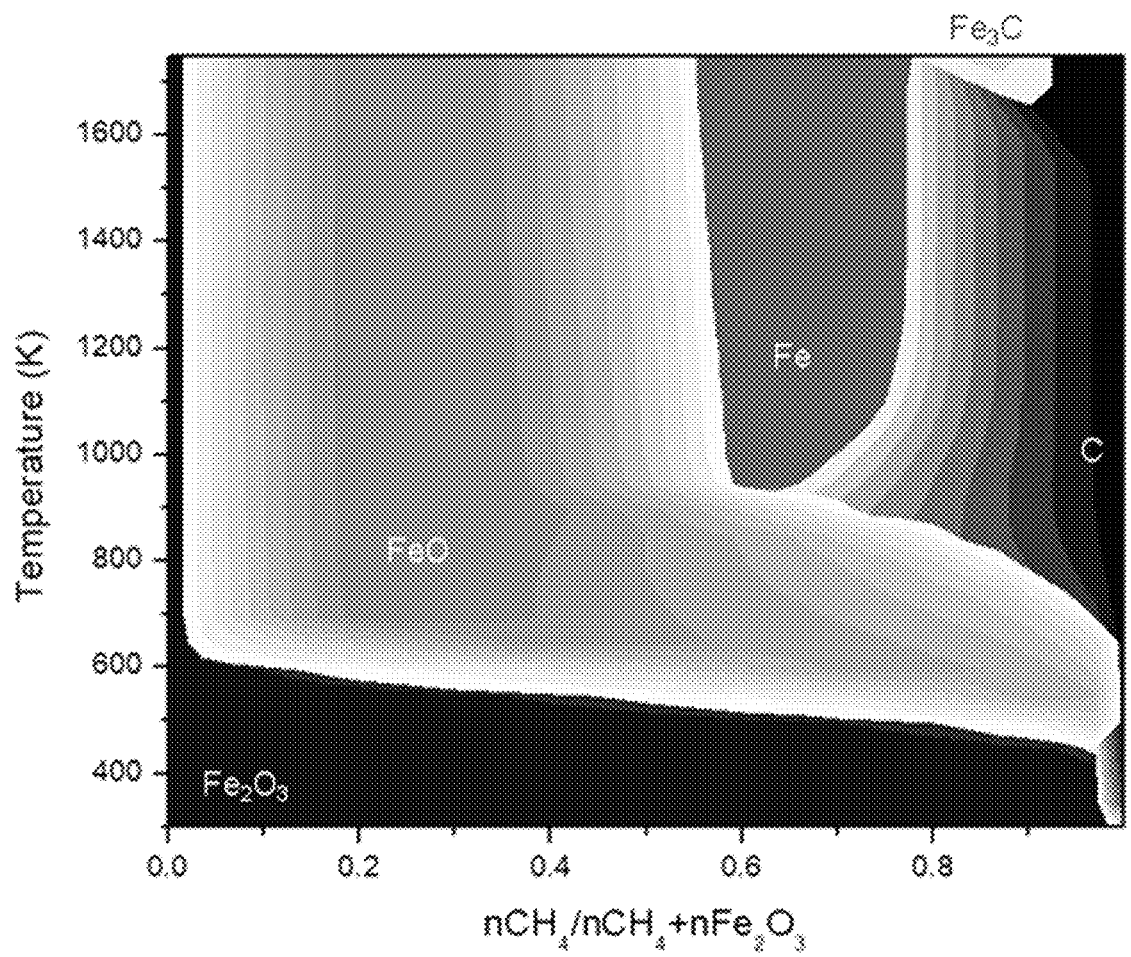
FIG. 16 is a phase diagram for solid species of iron in the fuel reactor.
Figure 17:
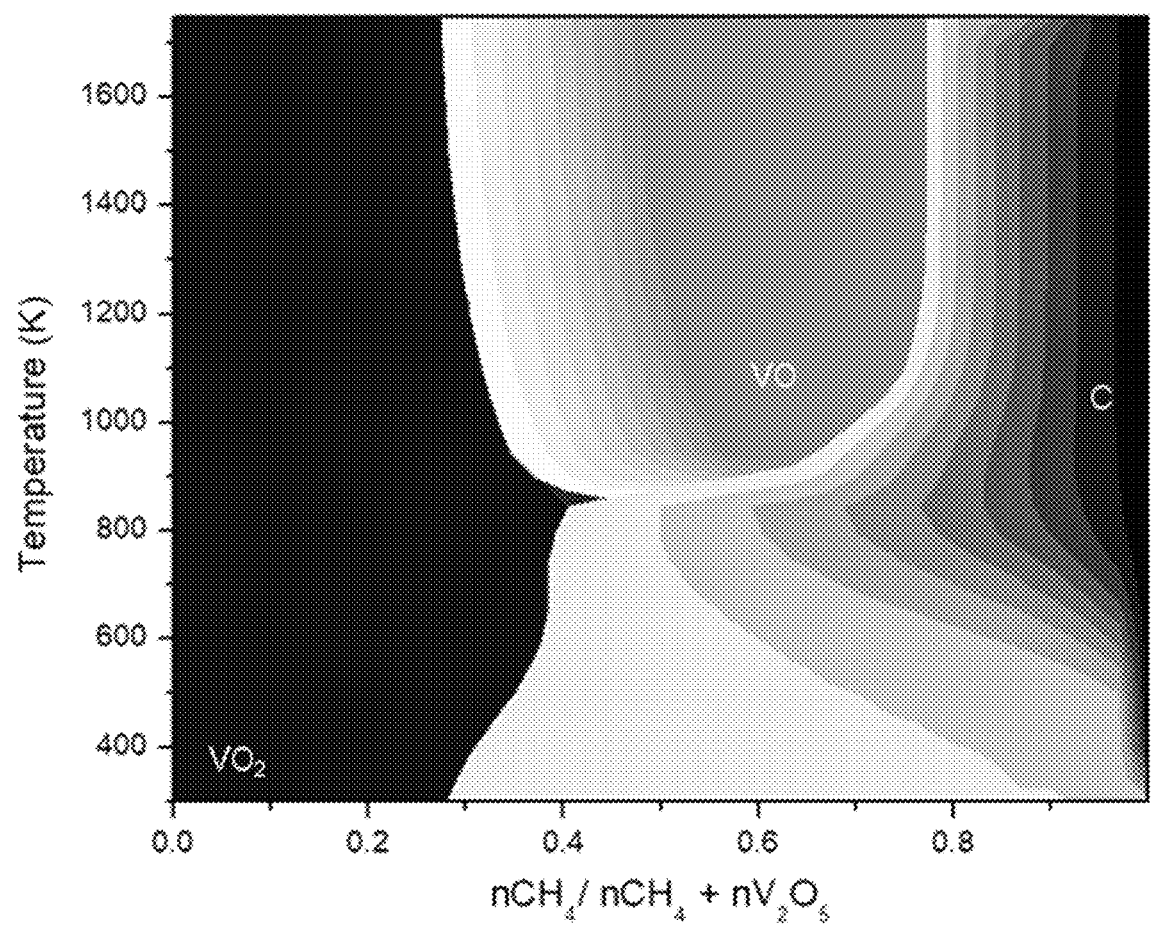
FIG. 17 is a phase diagram for solid species of vanadium in the fuel reactor.
Figure 18A:
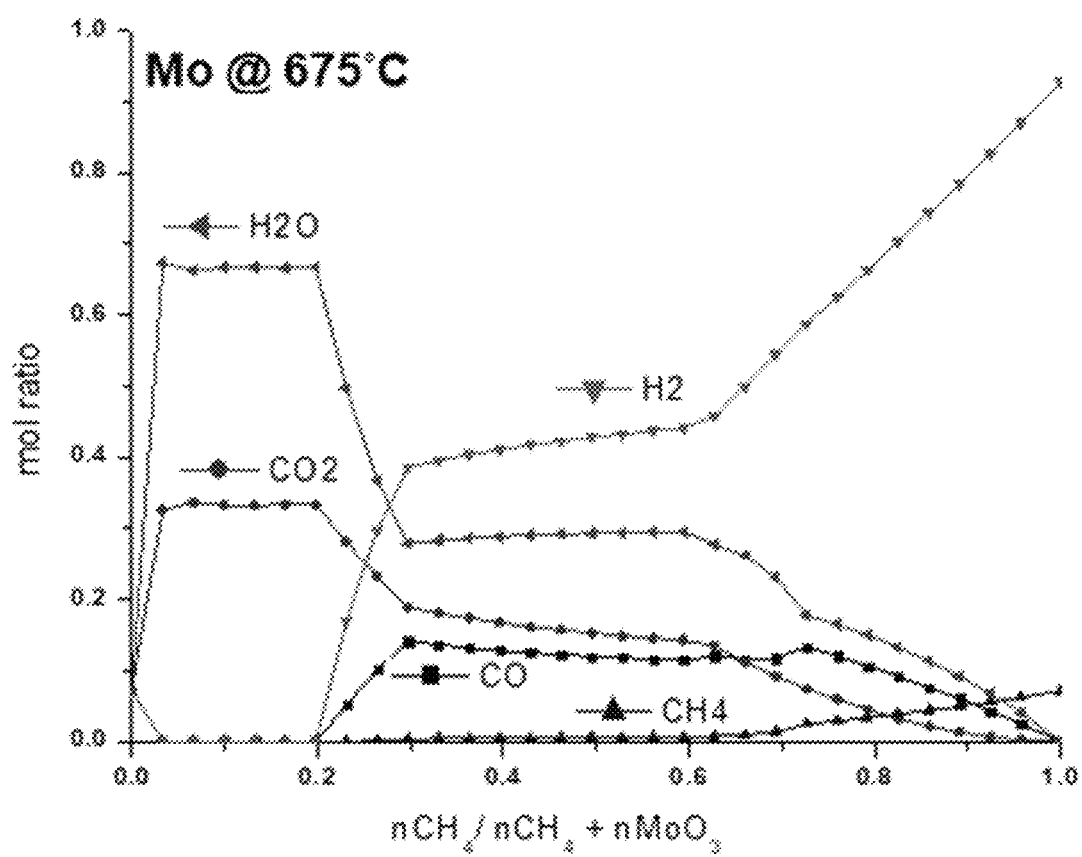
FIG. 18($a$) is a gas composition plot of mol ratio of gas vs. ($nCH_4/nCH_4+n$(metal oxide)) generated by the fuel reactor for metal oxides of molybdenum at 675° C.
Figure 18B:
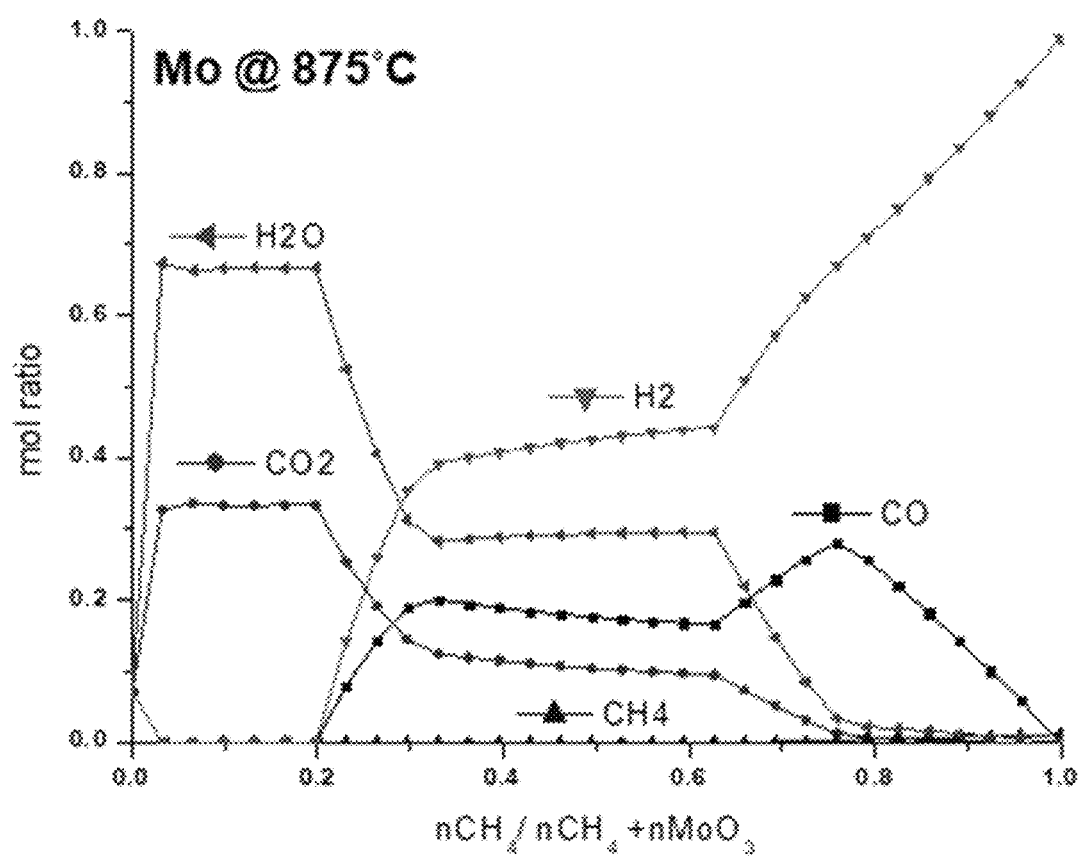
Figure 18C:
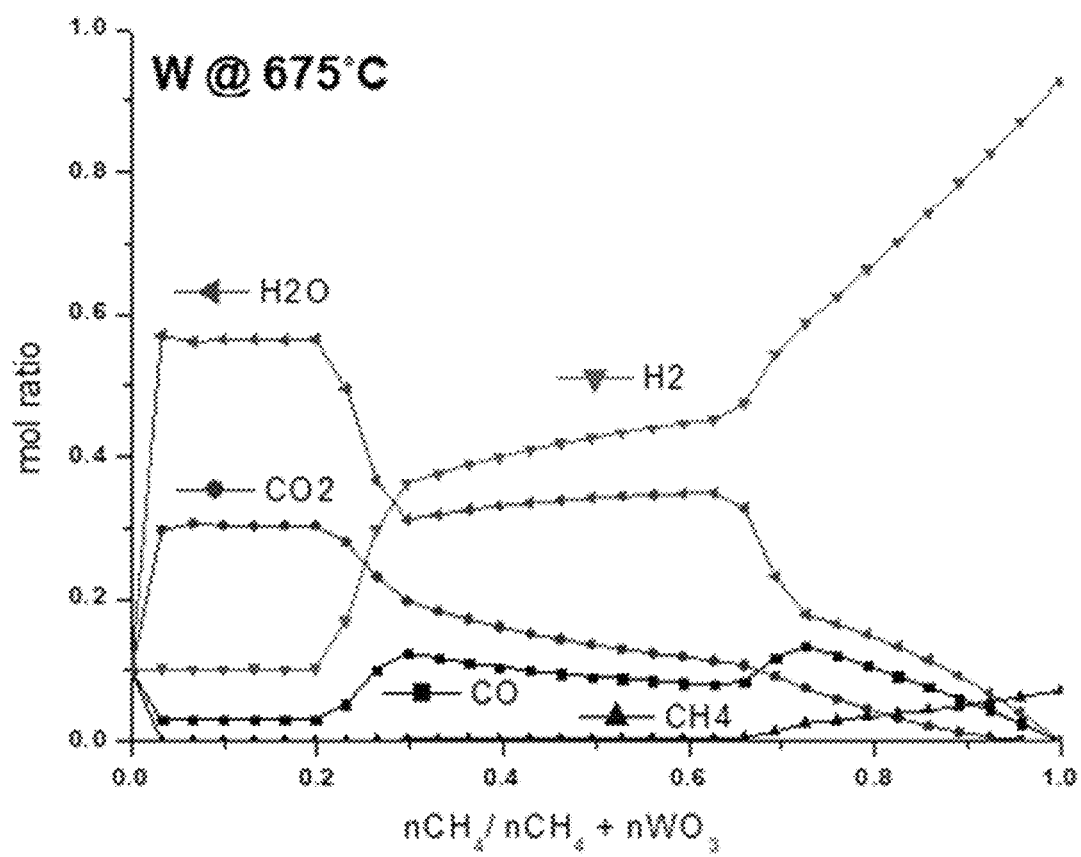
Figure 18D:
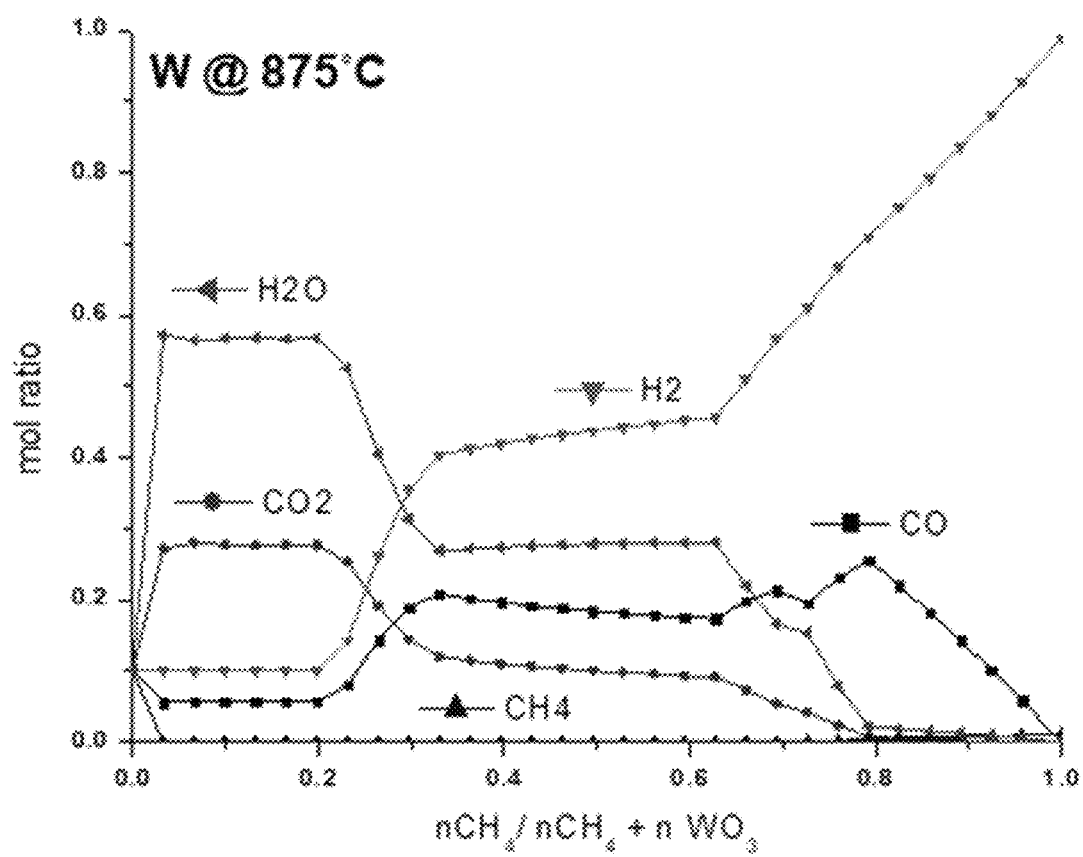

FIG. 6 shows the formation of different species during the oxidation of $Mo_2C$ in the air reactor. $Mo_2C$ is converted to MoC, Mo, $MoO_2$ and $MoO_3$ depending on the temperature of operation and the molar amount of air provided. Formation of nitride is not favorable. The phase diagrams for other transition metals are shown in FIGS. 7-17 (for some of the transition metals, diagrams for both the fuel reactor and the air reactor are included in the series, while for other transition metals, only the phase diagram for the fuel reactor is shown). FIG. 7 shows the formation of different manganese species in the fuel reactor, where it is seen that $MnO_2$ can be reduced using $CH_4$ to MnO, C or $Mn_3C$. The optimal region for manganese carbide ($Mn_3C$) formation is a ratio range of ($nCH_4/nCH_4+MnO_2$) between about 0.528 to about 0.693 and a temperature range between about 825° C. to about 1475° C. FIG. 8 shows the formation of different species during the oxidation of $Mn_3C$ in the air reactor. $Mn_3C$ can be converted to MnO, $MnO_2$, and C depending on the temperature of operation and the molar amount of air provided. Formation of nitride is not favorable. FIG. 9 shows the formation of different tungsten species in the fuel reactor, where it is seen that $WO_3$ can be reduced by $CH_4$ to $WO_2$, W, C, WC and $W_2C$. The optimal region for tungsten carbide (WC) formation is a ratio range of ($nCH_4/nCH_4+WO_3$) between about 0.627 to about 0.792 and a temperature range between about 525° C. to about 1125° C. FIG. 10 shows the formation of different species during the oxidation of WC in the air reactor. WC can be converted to $W_2C$, W, $WO_2$, $WO_3$ and C depending on the temperature of operation and the molar amount of air provided. FIG. 11 shows the formation of different zirconium species in the fuel reactor, where it is seen that $ZrO_2$ can be reduced by $CH_4$ to Zr, C or ZrC. The optimal region for zirconium carbide (ZrC) formation is a ratio range of ($nCH_4/nCH_4+ZrO_2$) between about 0.528 to about 0.726 and a temperature range between about 675° C. to about 1475° C. FIG. 12 shows the formation of different species during the oxidation of ZrC in the air reactor. ZrC can be converted to $ZrO_2$ and C depending on the temperature of operation and the molar amount provided. However, nitride formation is favorable. In FIG. 13, it is shown that $TiO_2$ can be reduced to C or TiC in the fuel reactor. However, the formation of the carbide only occurs at very high temperatures greater than 1000° C. which makes the process unreasonable for a commercial point of view. For this reason, titanium has a lower priority as a candidate for a CCLR process. In FIG. 14, it is shown that $Ta_2O_5$ can be reduced to C or TaC in the fuel reactor. However, the formation of the carbide only occurs at very high temperatures greater than 1000° C. which makes the process unreasonable for a commercial point of view. For this reason, tantalum has lower priority as a material for a CCLR process. In FIG. 15, it is shown that NiO can be reduced to Ni, C and $Ni_3C$ in the fuel reactor. However, the amount of $Ni_3C$ generated in the solid phase is low and the solid mix will predominately be C and Ni. For this reason, nickel is a lower priority transition metal candidate for a CCLR process. In FIG. 16, it is shown that $Fe_2O_3$ can be reduced to FeO, Fe and C in the fuel reactor. A very small amount of carbide is produced at very high temperatures and at those conditions a great amount of carbon is present. For these reasons, iron is a lower priority transition metal candidate for a CCLR process. In FIG. 17, it is shown that $V_2O_5$ can be reduced to $VO_2$, VO or C in the fuel reactor. No carbide is produced. For this reason, vanadium is not an appropriate transition metal candidate for a CCLR process.

Returning now to the summary phase equilibrium diagram of FIG. 4, it is shown that if the process temperature is restricted to temperatures at or below 1000° C., titanium and tantalum will not be suitable for CCLR because their carbide derivatives are only formed at very high temperatures, as also noted above. Ostrovski and Zhang [11] have shown that the reduction of $TiO_2$ with $CH_4$ is achieved at temperatures higher than 1250° C., when using high concentrations of $H_2$ to facilitate the reduction. When increasing the concentration of $CH_4$, it was observed that there was a great amount of carbon being formed, which was detrimental with respect to carbide formation. These experimental results are confirmed by thermodynamic predictions (see FIG. 13). York et. al [18] used a mixture of $CH_4/H_2$ to reduce $Ta_2O_5$ and carbide formation was observed at temperatures higher than 1223 K. When using $C_2H_6$ as a reducing agent, no carbide formation was observed under the experimental conditions studied. These data confirm the thermodynamic predictions. Once under a pure stream of $CH_4$, higher temperatures are required to achieve the reduction of the $Ta_2O_5$ into carbide.

NiC is formed at very low concentrations and when it is formed, the major component of its solid phase is C, making this metal impractical for the CCLR process (see FIG. 15), for this reason it is not represented in FIG. 4. $Fe_3C$ forms at very high temperatures and at very low concentrations in the solid phase. Therefore, it cannot be considered appropriate for proposed process (see FIG. 16) and is not being represented in FIG. 4. VC will not be formed under any of the conditions and was excluded from further investigation (see FIG. 17). Conclusively, the metal oxides which could be reduced to carbides under appropriate conditions are Mo, Mn, W, and Zr. As a result, the oxides of Mo, Mn, W, and Zr were studied under oxidation conditions in the air reactor (FIGS. 6, 8, 10, and 12).

Following an investigation of the solid phases of both reactors, the list of candidate metals was narrowed for further investigation. An important criterion is the formation of syngas and this requires an analysis of the gas phase. FIG. 18(a)-FIG. 18(d) show the gas compositions generated by the most promising transition metals Mo and W at 675° C. and 875° C. These temperatures represent the lowest and highest temperatures for common temperature ranges for Mo and W, respectively. The region where carbides are formed is within a ratio range of ($nCH_4/nCH_4+n(metal\ oxide)$) of about 0.6 to about 0.9. At the lower temperature of 675° C., for both metal oxides, there is a greater molar amount of $H_2$ (about 50% to 70%) followed by $H_2O$ (15% to 40%), CO (5% to 15%), $CO_2$ (2.5% to 15%), and some $CH_4$ (0% to 5%) in the gas stream. At the higher temperature of 875° C. $H_2$ remains the major component in the stream (50% to 80%), however formation of CO increases at higher temperatures (10% to 30%) whereas formation of $H_2O$ and $CO_2$ decrease (2.5% to 40% and 0% to 15%, respectively). Additionally, the presence of $CH_4$ is essentially eliminated, suggesting the possibility that $CH_4$ is fully converted. A typical syngas composition according to [19], [20] can vary depending on the feedstock, reactor and conditions, and is about 16-45% $H_2$, 26-60% CO, 4-20% $CO_2$, 0-5% $CH_4$ and $H_2O$. Therefore, the CCLR process using Mo and W oxides, which generate a greater percentage of $H_2$ could be applied for $H_2$ production.

Figure 19:
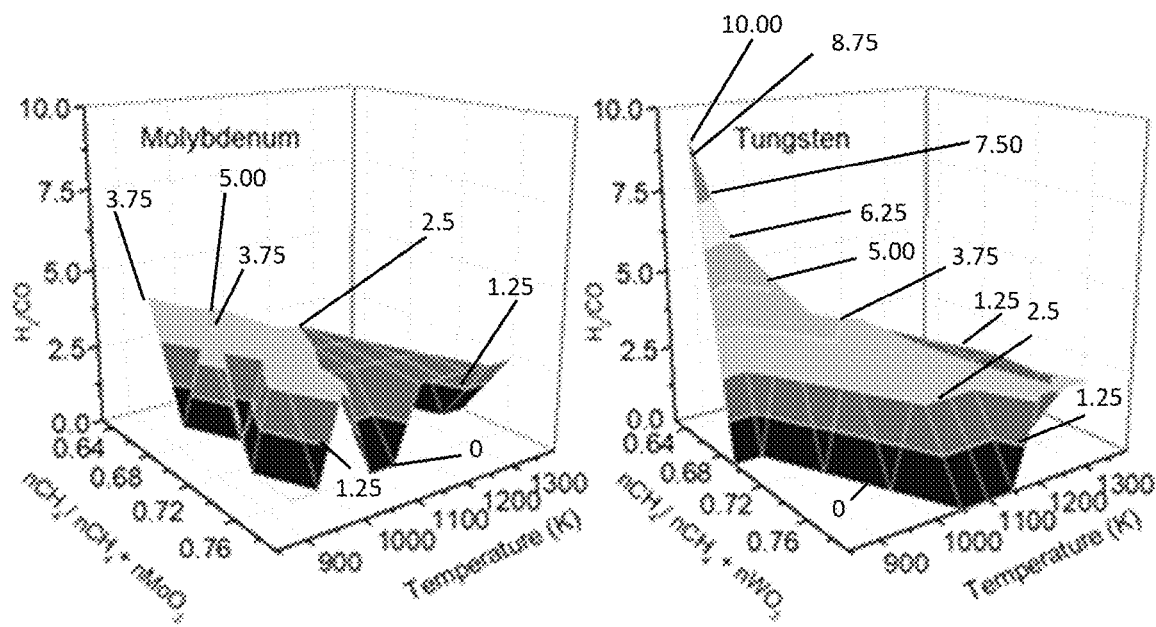
FIG. 19 includes 3-D plots of the $H_2/CO$ ratio for $MoO_3$ and $WO_3$ in the carbide-forming region with dependence upon temperature and ($nCH_4$ $nCH_4+n$(metal oxide)). The labelled values represent boundary values of the $H_2/CO$ ratio.
Figure 20A:
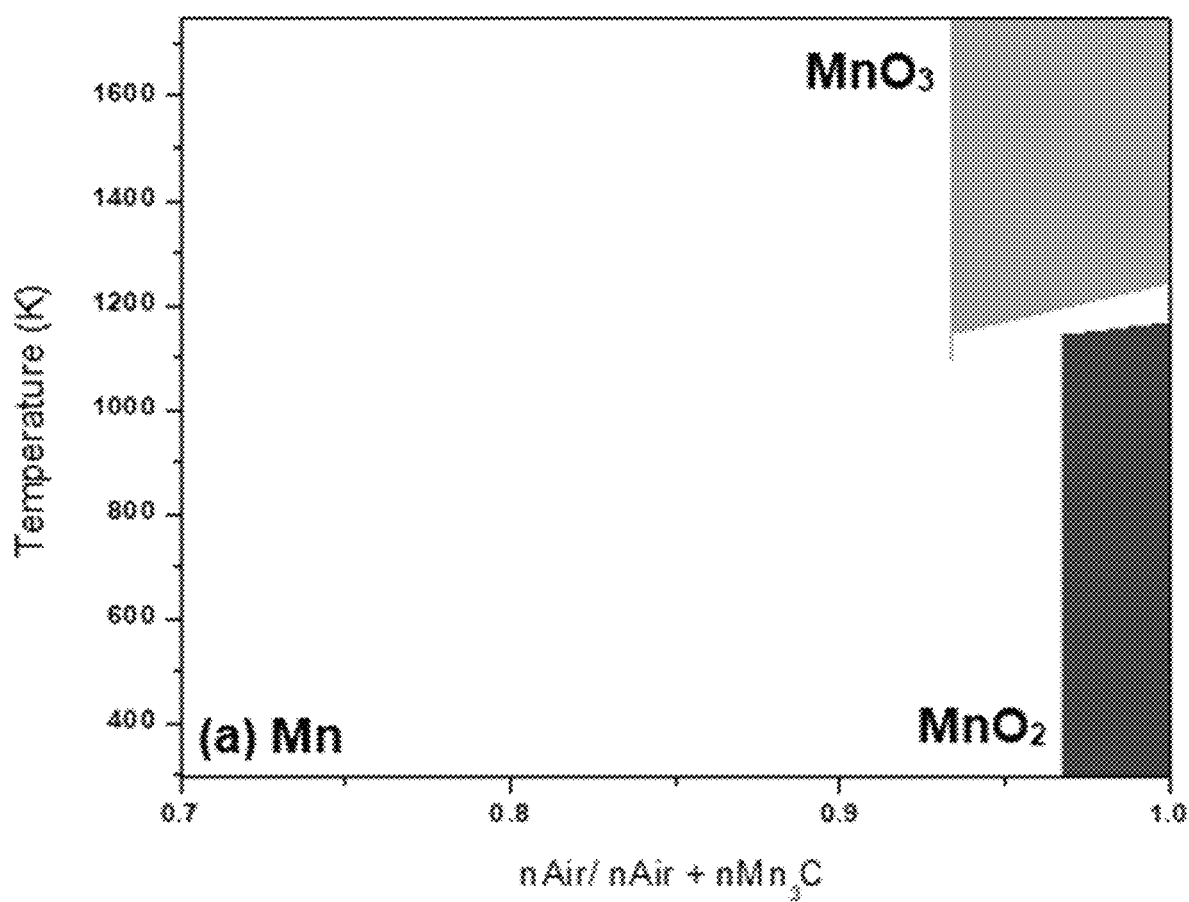
FIG. 20($a$) to FIG. 20($d$) show a series of plots for metal oxide formation in the air reactor from $Mn_3C$ FIG. 20($a$), ZrC FIG. 20($b$), $Mo_2C$ FIG. 20($c$), and WC FIG. 20($d$).
Figure 20B:
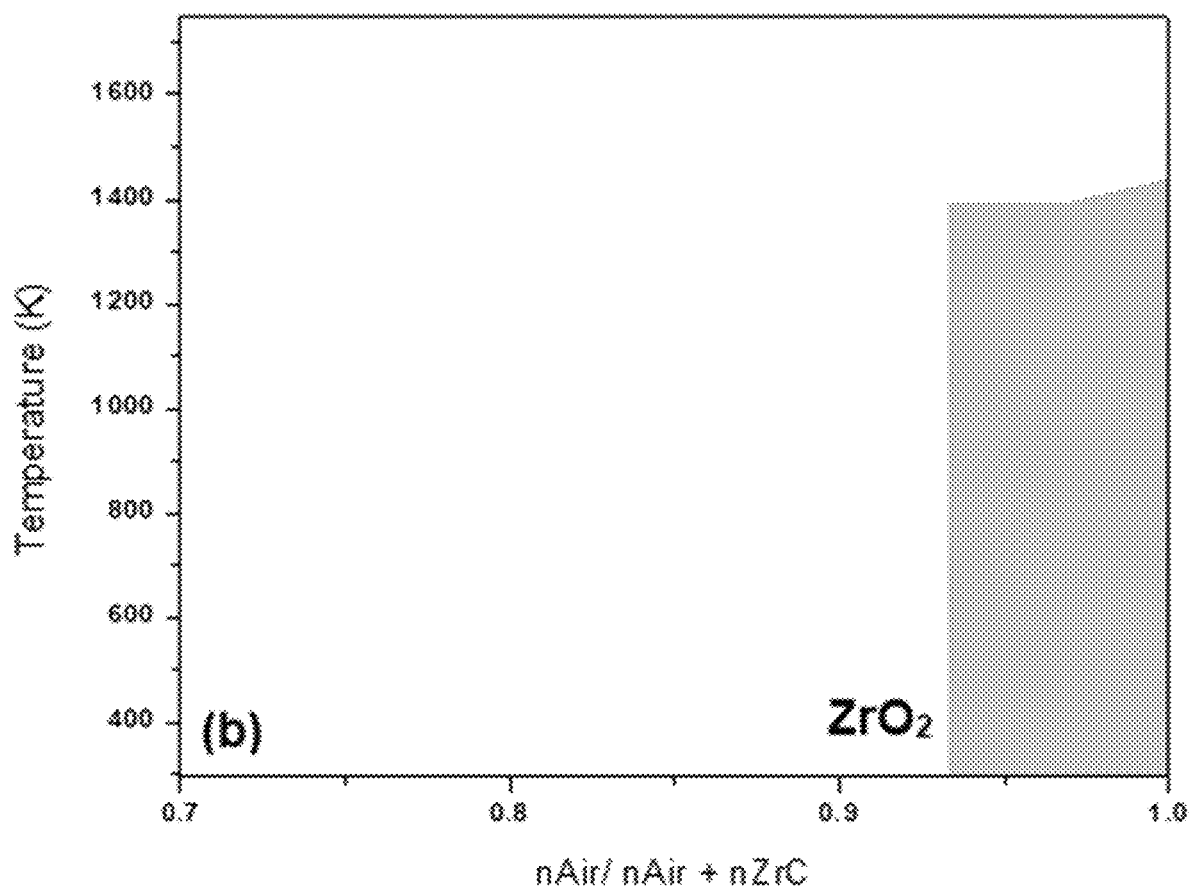
Figure 20C:
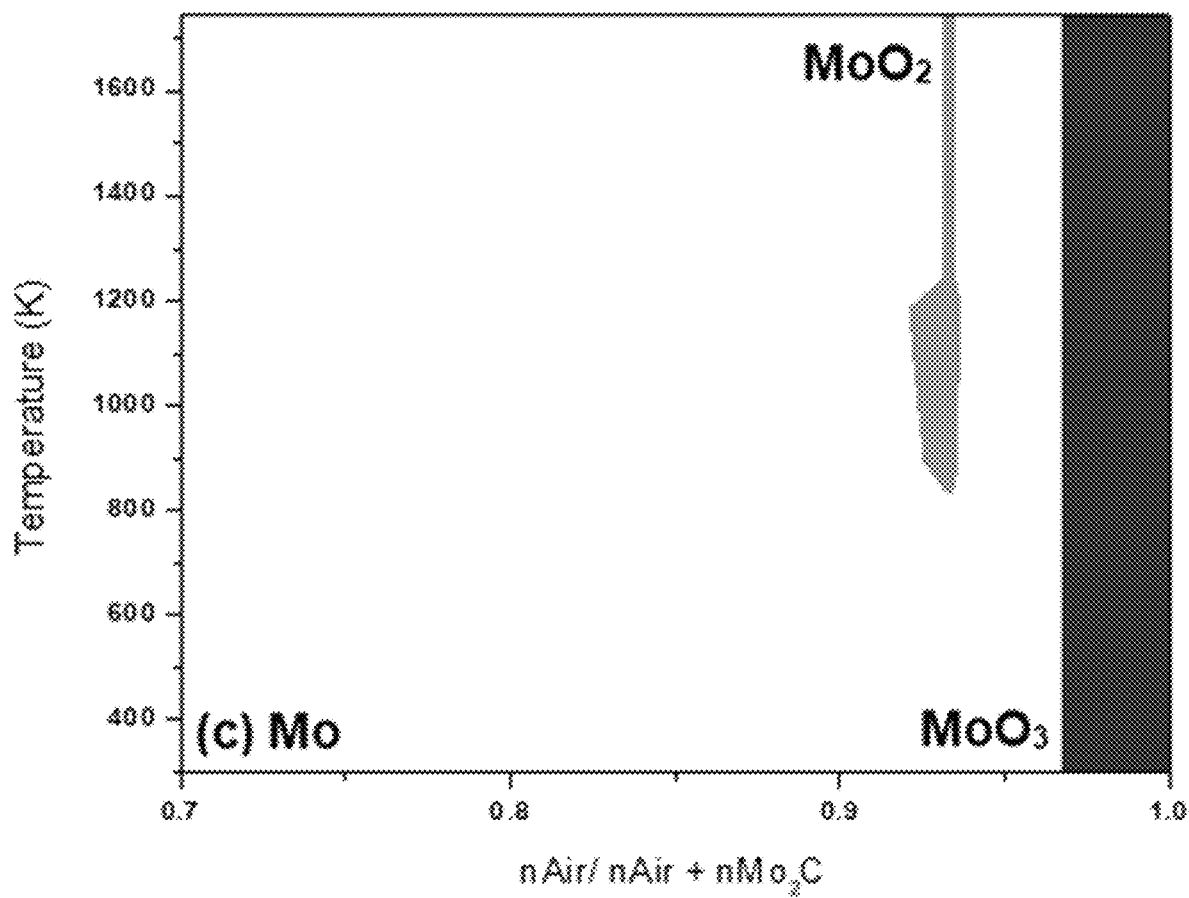
Figure 20D:
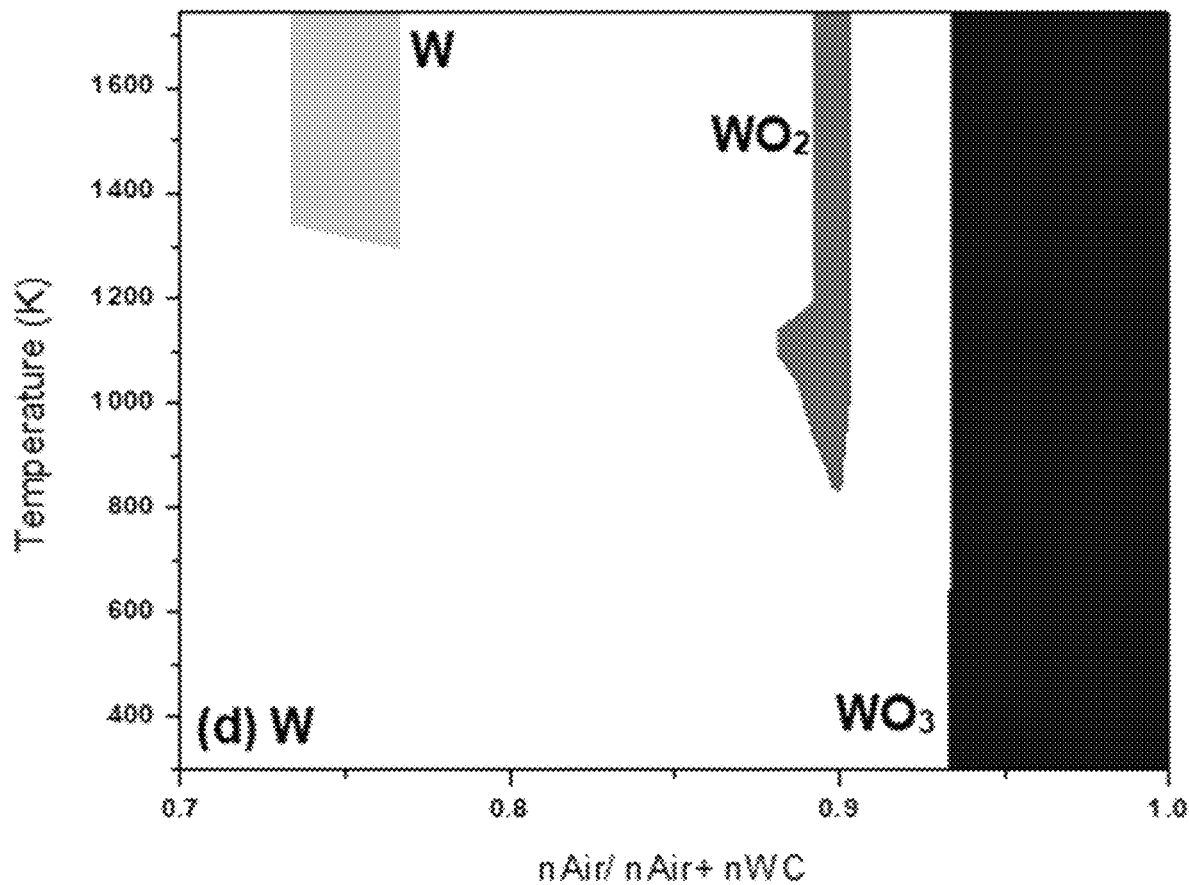

One of the most important characteristics to be evaluated for syngas is the $H_2$/CO ratio. This ratio classifies the quality of syngas that it is being produced by the process and according to its classification it can be applied to certain downstream process in a chemical plant. A $H_2$/CO ratio ranging from 0.6 to 2 is applied to most Fischer-Tropsch processes and methanol production. Ratios higher than 3 are used in production of $H_2$ production because of the high $H_2$ content [4], [21]. FIG. 19 includes 3-D plots of the $H_2$/CO ratio for molybdenum and tungsten in the carbide-forming region with dependence upon temperature and ($nCH_4/nCH_4+n(metal\ oxide)$). The lowest $H_2$/CO ratio predicted is 2.31 for molybdenum at 1125° C. The highest $H_2$/CO value is 9.34 for tungsten at 575° C. When comparing the two plots, it is seen that W provides a greater range of $H_2$/CO ratios. This finding indicates that a CCLR process using $WO_3$ may also be directed towards $H_2$ production while also providing lower $H_2$/CO ratios under different conditions which would be appropriate for production of gas streams for other applications which may be focused on production of syngas for direct use, for example. The apparent greater flexibility provided by a CCLR process using $WO_3$ relative to $MO_3$ led to further investigations focusing on $WO_3$.

Air Reactor-Oxygen carrier regeneration—Shown in FIG. 20 is a summary diagram indicating the conditions where the oxide formation in the air reactor is favorable for carbides of Mn, Zr, Mo and W, while they are the only species in the solid phase (see also FIGS. 6, 8, 10 and 12). Significant quantities of air are required necessary to generate the metal oxides, accounting for almost 90% mol ratio for Mn, Zr and Mo (see FIG. 20a-c). However, W showed can form oxides with slightly less air (see FIG. 20d). In some cases, the metals considered are oxidized to different states. WC can also be oxidized to its metal state at high temperatures. Limiting the process to 1000° C., it is possible to see that all the promising metal oxides considered can be formed within specific conditions. Moreover, nitride species were considered as possible species to be formed while in contact with the $N_2$ from the air. Only ZrC was found to generate nitride in the air reactor (see FIG. 12). Based on the possibility of ZrC forming nitrides during its oxidation with air, it was decided to exclude Zr as a candidate transition metal for CCLR. However, there is no experimental data or evidence at this stage which definitively shows that shows that zirconium nitrides can be formed under the studied conditions. Therefore, it may worth reconsidering zirconium as a candidate for CCLR in the future.

Since CCLR is a process that will be operated at high temperatures (above 600° C.), it is important to evaluate the melting point of the possible candidates in order to avoid early sintering of the materials. Table 1 summarizes the melting points of chemical species generated during the process. Species such as $MoO_3$ and $MnO_2$ have lowest melting points; 795° C. and 535° C., respectively. Depending on the temperature which the process will be operated these transition metal oxides may cause process issues. Based on the thermodynamic predictions from the fuel reactor $Mn_3C$ can be only formed in temperatures higher than 825'C and $MnO_2$ would be expected to melt at this temperature. Therefore, it was decided to exclude Mn from further investigations, leaving Mo and W as the remaining candidates.

TABLE 1

Melting Points of Species Formed During CCLR

| Species | Melting Point (° C.) | Species | Melting Point (° C.) |
|---|---|---|---|
| Mo | 2623 | $MoO_2$ | 1100 |
| MoC | 2577 | | |
| $Mo_2C$ | 2522 | $MoO_3$ | 795 |
| $W_2C$ | 2785 | $WO_3$ | 1473 |
| WC | 2776 | | |
| Zr | 1852 | $ZrO_2$ | 2677 |
| ZrC | 3417 | | |
| Mn | 1246 | MnO | 1945 |
| $Mn_3C$ | 1520 | $MnO_2$ | 535 |

Following evaluation of the gas composition produced by the fuel reactor, it is also important to evaluate the composition of the gas phase produced by the air reactor. In the oxide-generating region for Mo, the gas composition resulting is CO from 0% to 4%, $CO_2$ from 0% to 5%, $O_2$ from 0% to 21% and $N_2$ from 79% to 91%. For W there is no generation of CO under any of the conditions and the generated $CO_2$ ranges from 0%-9%. The generated $O_2$ ranges from 0% to 21% and the generated $N_2$ varies from 79% to 90% for W. There was no scenario within the studied conditions where NOx products were formed in the air reactor. Oxidation could also be carried out with pure $O_2$ generating a pure stream of CO and/or $CO_2$. The stream of CO and $CO_2$ can be routed to a second fuel reactor where the carbide is already formed. Carbides have proven to be good catalysts for dry reforming, which could further improve the $CH_4$ conversion [15], [16], [22]. Preliminary simulations show that the addition of $CO_2$ in the feed does not improve formation of the carbide, which indicates that the species formed will be participating only in the dry reforming reactions, as suggested. Therefore, this possibility requires further investigation. Considering that a pure stream of $CO_2$ would benefit the dry reforming reactions, W appears to be the best candidate transition metal for this application because CO is not produced in the air reactor.

Figure 21:
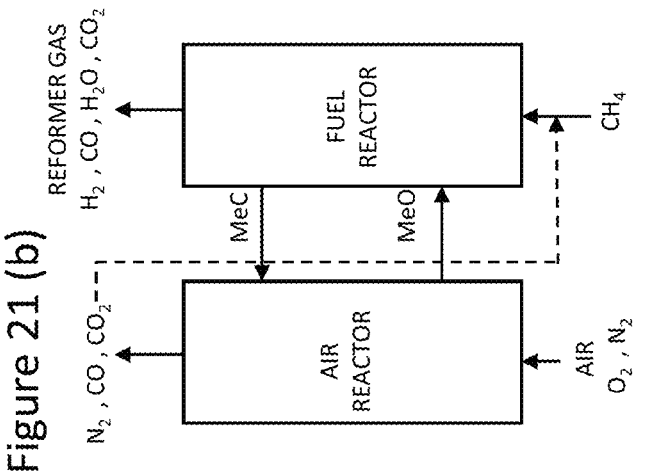
FIG. 21($a$) is an embodiment of transition metal carbide chemical looping reforming (CCLR) with fuel reactor input of only $CH_4$ and providing gas streams from the fuel reactor and the air reactor.
Figure 21:
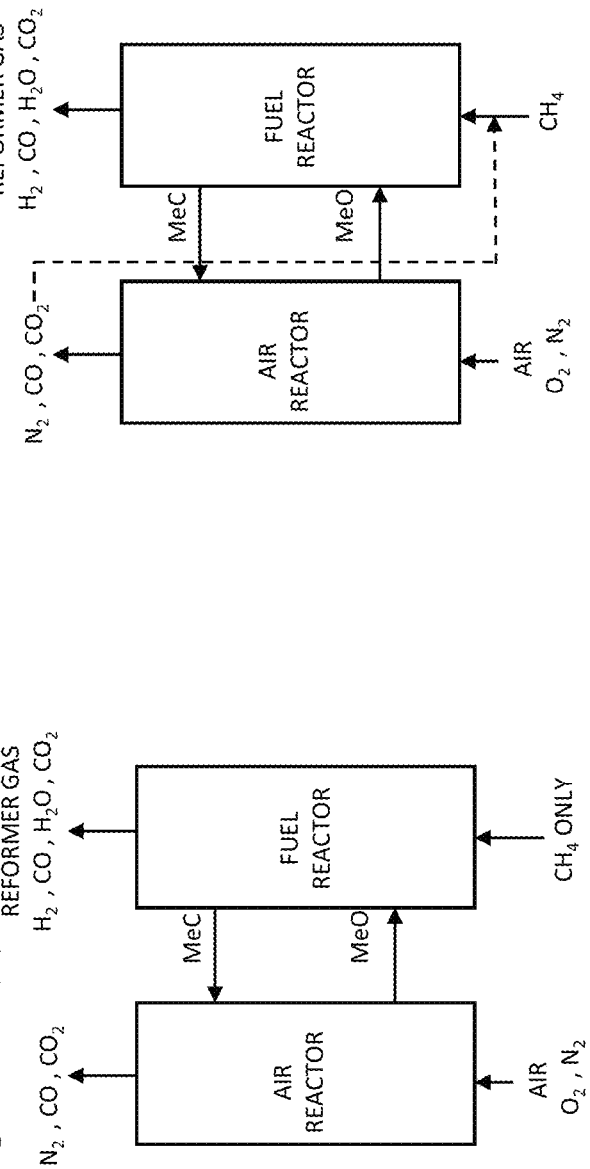
Figure 22A:
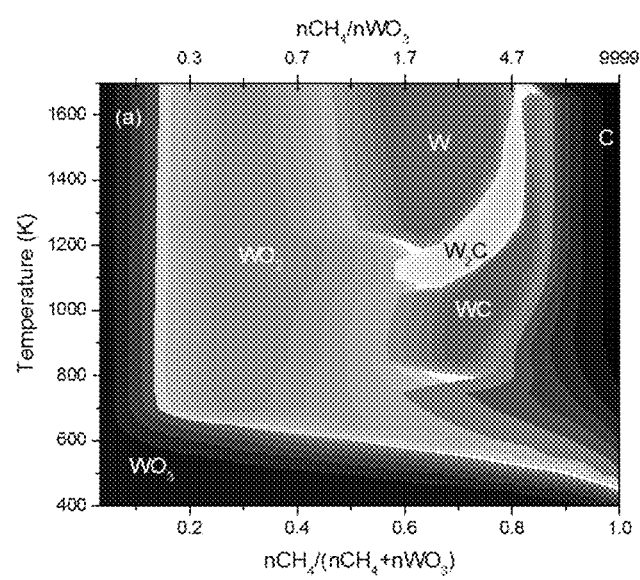
FIG. 22($a$) shows molar fraction stability fields for oxidation states of tungsten in the fuel reactor fed with only $CH_4$.
Figure 22B:
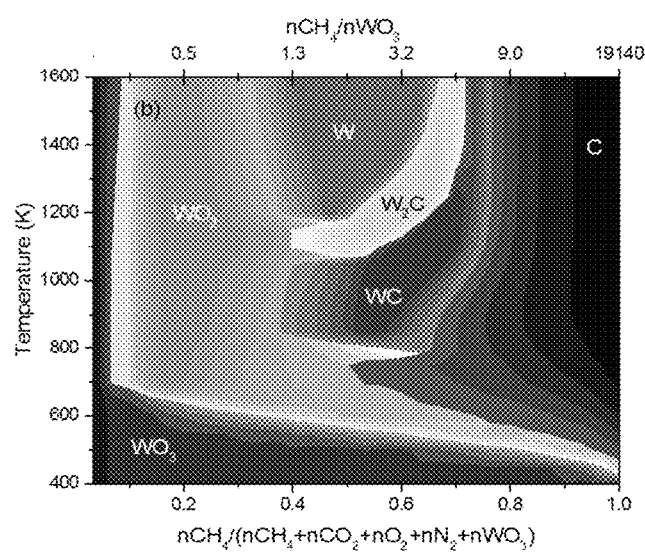

Routing of the Output Stream of the Air Reactor to the Input Stream of the Fuel Reactor in a Zero-Net Emission Process—The effect of the mixing the gas stream from the air reactor outlet with fresh $CH_4$ at the fuel reactor inlet (FIG. 21(b)) was evaluated at thermodynamic equilibrium for the tungsten system. For 1 mol of WC fed into the air reactor, it was estimated that for full re-oxidation to $WO_3$ the flue gas will be 9.4 mol % $CO_2$, 0.5 mol % $O_2$ and 90.1 mol % $N_2$. This gas is co-fed into the fuel reactor in a mixture with fresh $CH_4$ to eliminate unwanted $CO_2$ emissions. This system was evaluated with a control tungsten system having a fuel reactor input of only $CH_4$ as depicted in FIG. 21(a). A comparison of the results of the processes of FIGS. 21(a) and 21b) is provided in FIGS. 22(a) and 22(b). Results indicate that the addition of $N_2$, $O_2$ and $CO_2$ to $CH_4$ in the fuel reactor provide a positive impact on carbide formation. It was determined that at equilibrium, $N_2$, $O_2$ and $CO_2$ enhance the formation of WC such that a slightly lower $CH_4/WO_3$ ratio is required to achieved full carburization towards WC ($CH_4/WO_3=1.94$ (FIG. 22(a)) versus $CH_4/WO_3=1.9$ (FIG. 22(b)) in the presence of $N_2$, $O_2$ and $CO_2$). The fuel reactor inlet requires greater than 65 mol % $CH_4$ to provide full carburization of $WO_3$. The observed behavior could be associated with initial dry reforming of $CH_4$ with $CO_2$ thereby producing $H_2$ which facilitates reduction of $WO_3$. Further analysis is necessary to validate this prediction.

Figure 23:
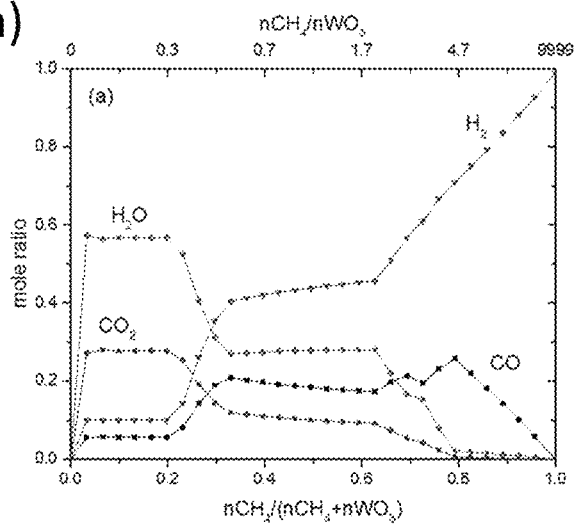
FIG. 23($a$) is the molar fraction profile for gas products in the fuel reactor at 1148 K (875° C.), fed with only $CH_4$.
Figure 23:
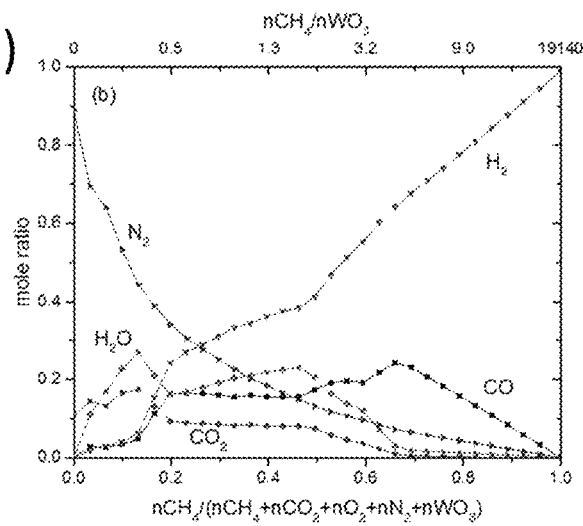

FIGS. 23(a) and 23(b) indicate the composition of the outlet gas in the two scenarios outlined above. As expected, the gas concentration profiles are modified in the combined feed (FIG. 23(b)) relative to the feed containing only $CH_4$ (FIG. 23(a)). The ratio of $H_2/CO$ as well as the $CO_2$ and $H_2O$ concentrations remain similar. However, $N_2$ levels in FIG. 23(b) may represent an additional challenge for separation of the desired products ($H_2$ or syngas) from the outlet stream.

Heat Demand and Supply—With the knowledge of the gas composition in the optimal regions for the fuel reactor and the air reactor, the range of possible reactions occurring in both reactors can be predicted. Table 2 summarizes the heat of reaction of the reactions under standard conditions. All reactions occurring in the fuel reactor are endothermic, requiring energy input into the reactor to drive the reactions. The reactions in the air reactor are exothermic and have potential to produce sufficient energy to drive the fuel reactor and possibly provide surplus energy to other areas within the chemical plant. A thorough investigation of mass and heat balance should be performed to evaluate the promising findings.

TABLE 2

CCLR Reactions [23]

| | | | $\Delta H°$ (kJ·mol$^{-1}$) |
|---|---|---|---|
| | Reactions Thermodynamic | | |
| Fuel Reactor | $4 WO_3 + CH_4 \rightarrow 4 WO_2 + 2 H_2O + CO_2$ | (1) | 210.50 |
| | $WO_3 + CH_4 \rightarrow WO_2 + CO + 2H_2$ | (2) | 217.56 |
| | $WO_2 + 3 CH_4 \rightarrow WC + 2CO + 6 H_2$ | (3) | 805.88 |
| | $CH_4 + 3 H_2O \rightarrow CO + 6 H_2$ | (4) | 206.20 |
| | $CH_4 + CO_2 \rightarrow 2 CO + 2 H_2$ | (5) | 247.34 |
| Air Reactor | $WC + 2 O_2 \rightarrow WO_2 + CO_2$ | (6) | -942.63 |
| | $WC + ½ O_2 \rightarrow WO_2 + CO$ | (7) | -659.64 |

TABLE 2-continued

CCLR Reactions [23]

| | | $\Delta H°$ (kJ·mol$^{-1}$) |
|---|---|---|
| $WO_2 + ½ O_2 \rightarrow WO_3$ | (8) | -253.22 |
| Reactions proposed by literature | | |
| $WO_3 + H_2 \rightarrow WO_2 + H_2O$ | (9) | 11.36 |
| $WO_2 + 2 CH_4 \rightarrow W + 2 CO + 4 H_2$ | (10) | 518.38 |
| $WO_2 + CH_4 \rightarrow W + CO_2 + 2 H_2$ | (11) | 271.04 |
| $2 W + CH_4 \rightarrow W_2C + 2 H_2$ | (12) | 48.51 |
| $W_2C + CH_4 \rightarrow 2 WC + 2 H_2$ | (13) | 20.06 |

Figure 24A:
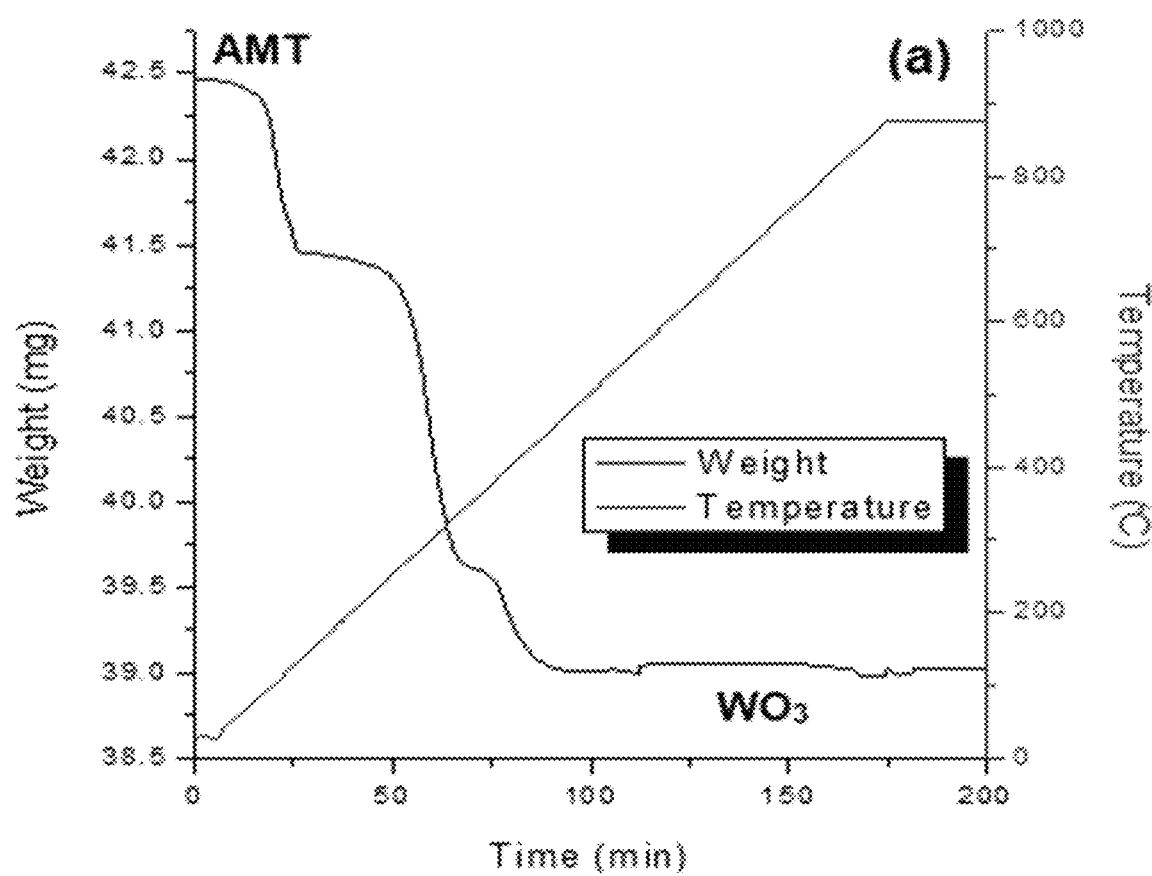
FIG. 24($a$) is a plot of decomposition of ammonium metatungstate (($NH_4)_6H_2W_{12}O_{40}.H_2O$) over time and increased temperature.
Figure 24B:
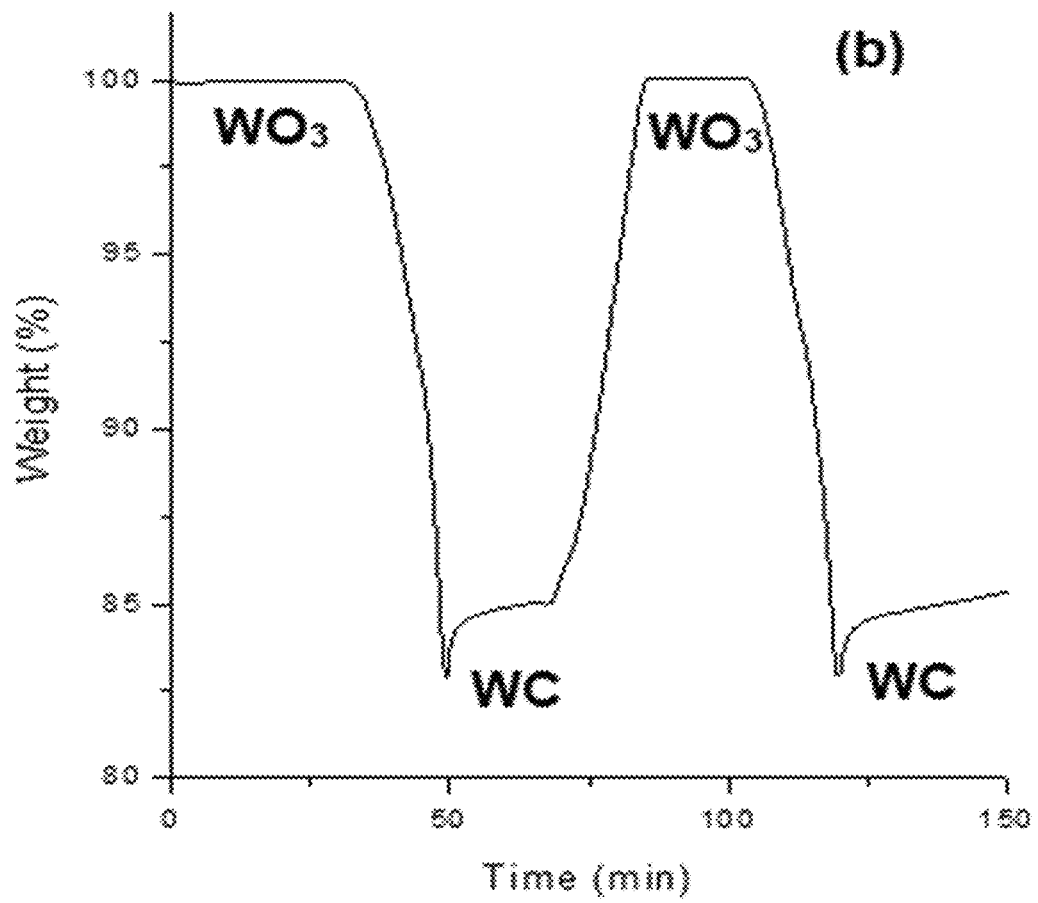
Figure 24C:
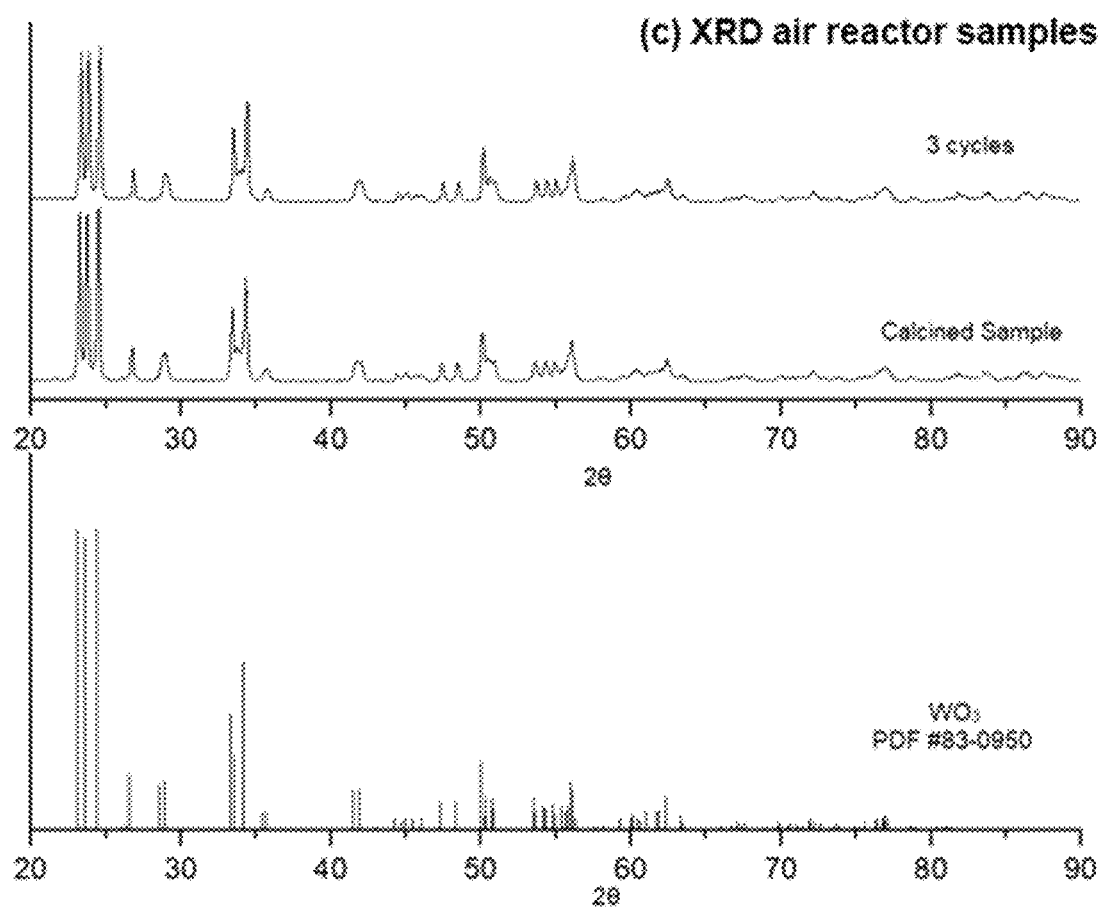
Figure 24D:
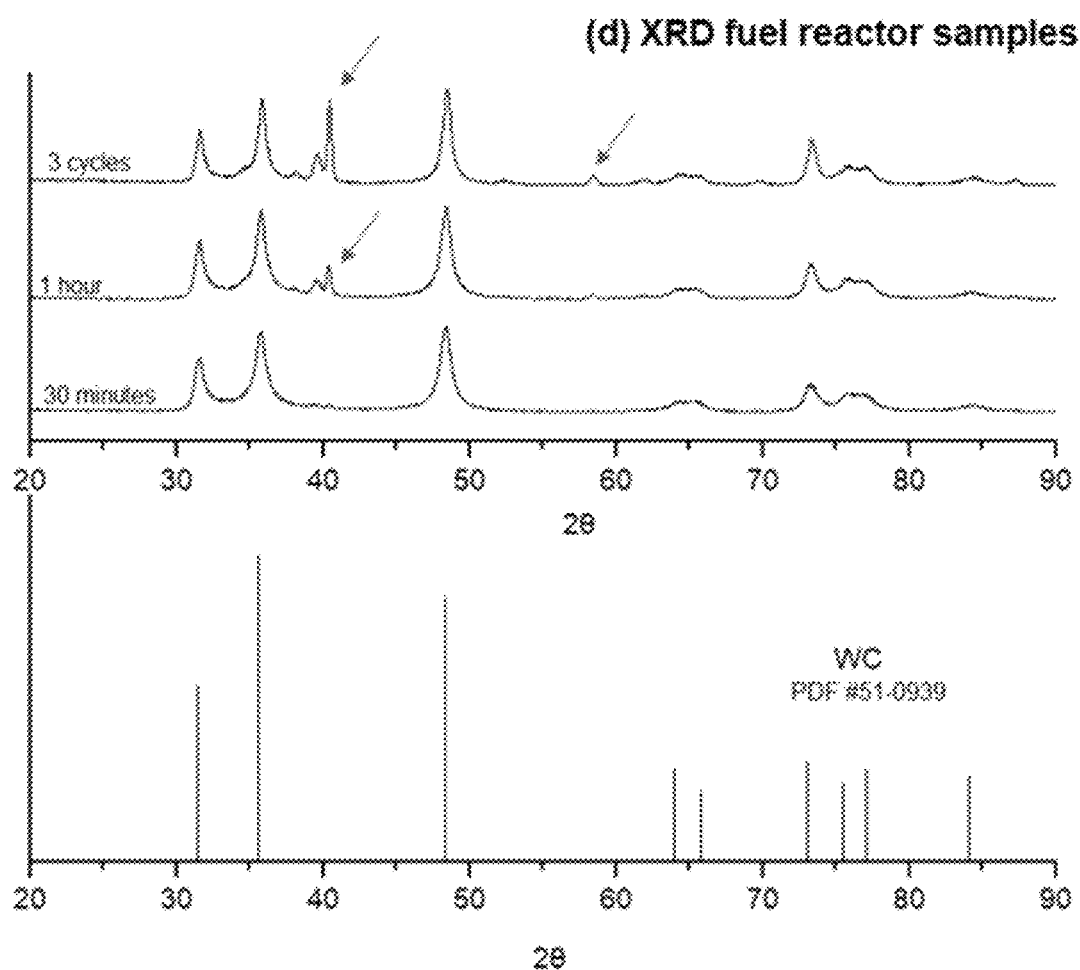

Experimental Verification—TGA-MS investigations of a CCLR process based on tungsten showed that it is possible to obtain $WO_3$ by only heating the metal precursor ammonium metatungstate under an $N_2$ atmosphere. FIG. 24(a) shows the decomposition of the metal precursor into $WO_3$ and the XRD results confirm formation of $WO_3$ (FIG. 24(c)). The decomposition steps follow the same route proposed by [24]. Once $WO_3$ was obtained from the precursor, the material was subjected to CCLR cycles. FIG. 24(b) indicates the weight gain or loss occurring during the redox cycles. The weight loss during reduction matches the formation of WC and an XRD analysis confirms the formation of this species (FIG. 24(d)). The weight gain during the oxidation also matches the formation of $WO_3$ and XRD analysis confirms the formation of this species. Each step has a duration of 30 min and a purge with $N_2$ between the redox steps. The stability of the material was tested in 5 cycles and the results show that while $WO_3$ is stable, the carbide may have two different species, WC and $W_2C$, being formed. Steps longer than 30 min result in formation of these two different carbide species. By the 3rd cycle formation of both carbide species was observed. These preliminary experimental results of the solid phase show that is possible to obtain WC and $WO_3$ during different cycles. It appears that oxides are very stable species and are fully regenerated during repeated cycles. On the other hand, with respect to the carbides, it will be necessary to obtain a more detailed understanding of the species being reduced if it is confirmed that different carbides are formed under similar conditions.

Energy Intensity and Carbon Emissions—Steam reforming processes generate $CO_2$ emissions due to fuel combustion used to generate steam. Collodi and Wheeler [25], estimated that a typical concentration of the $CO_2$ in the flue gas of the reformers is about 19%. In the case of CCLR as described herein, the $CO_2$ would only be produced in the air reactor in order to regenerate the oxygen carrier, with concomitant generation of energy necessary to supply the fuel reactor. When using tungsten in the CCLR process, the maximum concentration of $CO_2$ in the depleted air stream is estimated to be about 9%. When routing this stream of produced $CO_2$ to the fuel reactor, it will be converted into CO through a dry reforming reaction and the $CO_2$ emissions can theoretically be lowered to zero, providing a significant operational advantage. Abbas and Daud [26] have estimated that the energy efficiency of a typical SMR process is 83%. Further calculation is required to determine the energy efficiency of this process. In any case, CCLR has significant potential to achieve high energy efficiency because it is an autothermal process.

Figure 25:
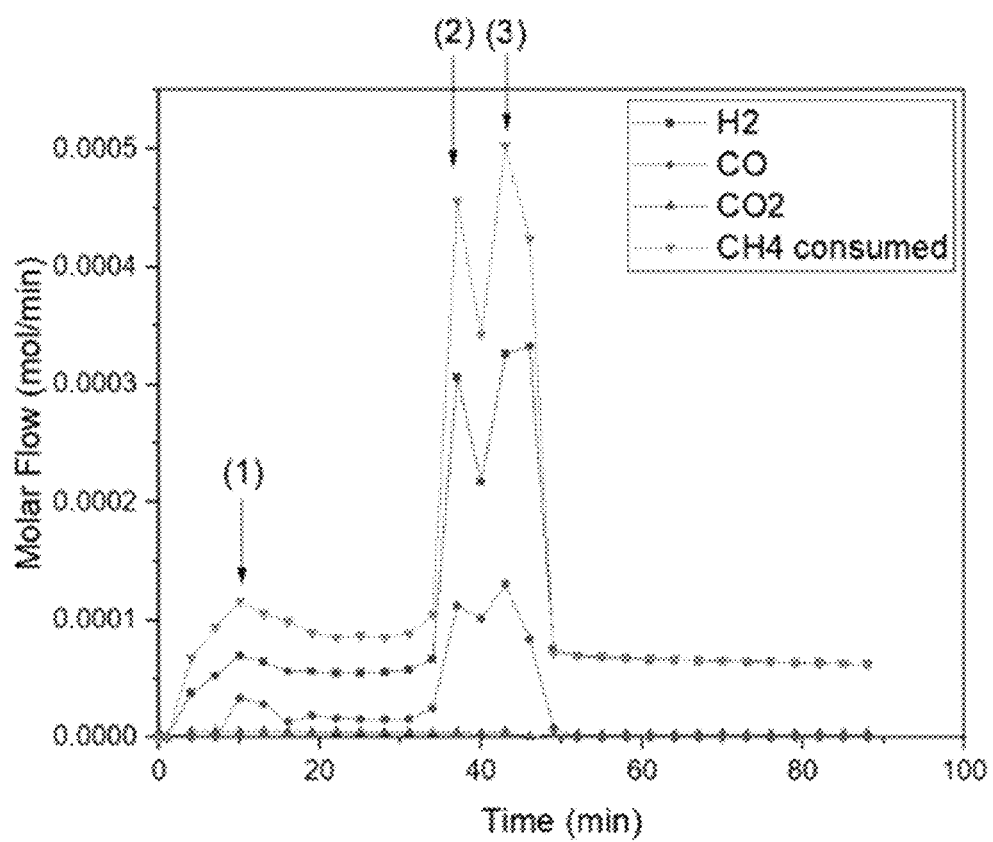
FIG. 25 is a plot of molar flow of products ($H_2$, CO and $CO_2$) and $CH_4$ consumed.

To verify that the cycling process is producing syngas a reactor set-up attached to a Micro-GC was used to measure the gas composition as well as a quadrupole mass spectrometer attached to the TGA. From the chromatograms generated, the gas composition was determined using the proper calibration. The results enabled the determination of the molar flow. A plot summarizing the molar flow of each specie with time is shown in FIG. 25, which indicates the gas composition through time when reducing 1 g of $WO_3$ with 60 mL·min-1 of 75 vol % $CH_4$ and 25 vol % $N_2$ at 800° C. The result reveals 3 peaks that correlate with 3 different steps of the reduction and following carburization step which was proposed previously [27]. The first peak relates to initial reduction of $WO_3$ to $WO_2$. The reactions involved in this stage are (2) and (9). This initial reduction is small because it reduces only the material exposed in the surface of the solid. Once the reactive gas has access to the material in the bulk, the second step of the reaction happens, and it represents the second peak. In this step $WO_2$ is reduced to W and W is carburized to $W_2C$ in reactions (10) and (12). In the third peak the carburization is complete by $W_2C$ being converted into WC in reaction (13). The results suggest that 18% of the oxide available was converted to WC while the remaining 82% was converted to $WO_2$. One of the reasons why the remaining $WO_2$ could not be converted to WC may be related to the presence of carbon being deposited on its surface. However, this hypothesis should be further investigated.

The result shows the $H_2$/CO ratio varying from 2 to 9 depending on the step of process, in accordance with the thermodynamic predictions. The gas analysis of the AR showed the presence of $CO_2$ and CO in the gas phase indicating that reactions (6) and (7) happen during the carbide oxidation. The mass balance calculations indicate that from the percentage of carbide formed, its oxidation was achieved in the AR. To further confirm the calculations, solid characterization should be conducted in the samples from the reactor at the different steps.

Figure 26:
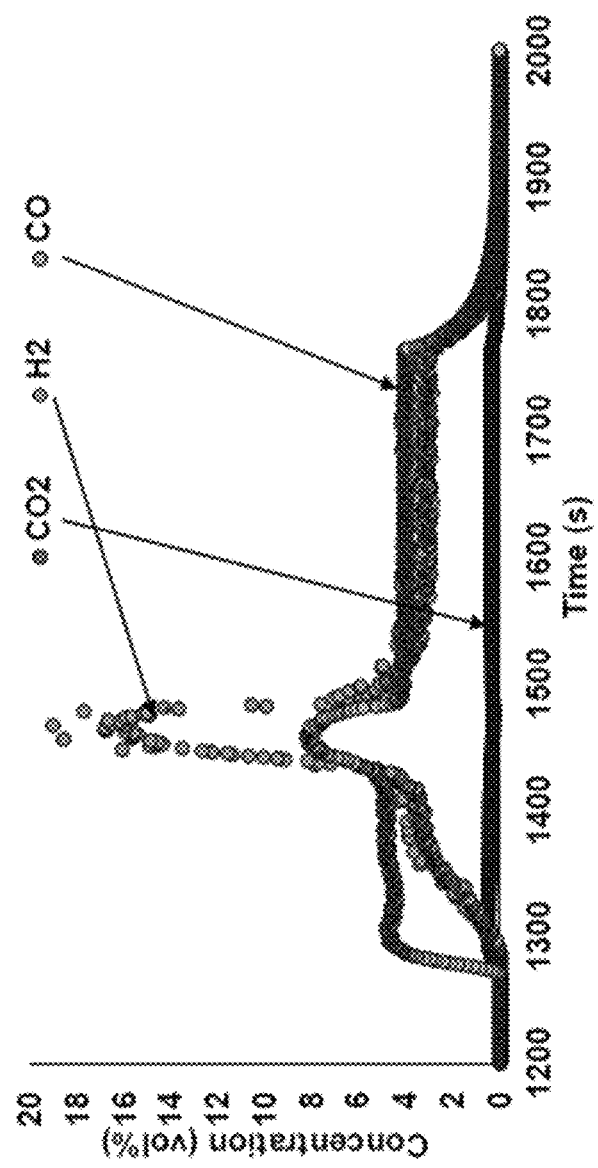
FIG. 26 is a plot of volume percentage of different species measured by the quadrupole mass spectrometer during the reduction step of CLLR.

Further investigation of the gas phase was performed using a quadrupole mass spectrometer. The reactions were performed under the same conditions of the experiment reported in FIG. 24(b) using the TGA. The results confirm the formation of $H_2$, CO and $CO_2$ (See FIG. 26). The findings show similar behavior as observed in the Micro-GC data, validating the previous conclusions.

Summary and Advantages of Carbide Chemical Looping Reforming—Conventional reforming technologies represent a significant share of the energy and carbon intensity in the production of hydrogen and syngas. The present inventors have herein described embodiments of an inventive process which is given the name "carbide chemical looping reforming (CCLR). The CCLR process is capable of producing $H_2$ and CO (syngas) or a gas stream predominantly including $H_2$ without the need of external energy sources (autothermal process) and with minimal carbon emissions. To accomplish this, CCLR uses the principle of cyclic oxidation and carburization of transition metals as oxygen carriers to produce the desired products with high selectivity while self-supplying the required energy for this transformation. CCLR uses (i) a fuel reactor where the oxygen carrier reacts with a fuel source (e.g. $CH_4$) to produce $H_2$ or syngas while carburizing the oxygen carrier, and (ii) an air reactor where the carburized oxygen carrier is regenerated to its oxidized form using air in an exothermic reaction that generates sufficient heat to drive the overall process. A thermodynamic equilibrium estimation indicates that the CCLR process permits a wide range of operation conditions to favor different products. Operation conditions of 800-1000 K and fuel/metal ratios greater than about 2 are suitable for $H_2$ and syngas production. A wide range of $H_2$/CO ratios between 1-10 in the gas output stream from the fuel reactor can provide the desired inputs for the Fischer-Tropsch process, as well as methanol, dimethyl ether and hydrogen production processes.

The gas stream from the air reactor can be routed to mix with the input fuel for the fuel reactor to eliminate carbon emissions. As a result of this process modification, enhancement of the carburization of the oxygen carrier is expected with minimal impact to the composition of the product stream from the fuel reactor. Preliminary experimental results confirm the existence of the oxygen carrier oxidation state transition predicted by the model.

CCLR is expected to provide a major contribution to the field of methane decarbonization and chemical synthesis by demonstrating the possibility of producing hydrogen or syngas without the need of external steam/$CO_2$ and heat.

EQUIVALENTS AND SCOPE

While some of the data presented herein are accompanied by remarks regarding the preferred use of certain transition metals over others in certain embodiments of the process, it is to be understood that these remarks should not be construed as limiting because they apply to the conditions described herein. It may be possible to develop other conditions which will be appropriate for use of most, if not all transition metals.

While the example embodiments described herein refer to a process using separate fuel and air reactors, the process may be conducted using alternative equipment wherein reactions are conducted in a plug flow reactor with an internal recirculation fluidized bed as described in U.S. Pat. No. 10,315,176, incorporated herein by reference in its entirety. Furthermore, the gas streams can be automatically switched to change gases from an oxidative environment to a reducing environment without moving the transition metal.

Other than described herein, or unless otherwise expressly specified, all of the numerical ranges, amounts, values and percentages, such as those for amounts of materials, elemental contents, times and temperatures, ratios of amounts, and others, in the following portion of the specification and attached claims may be read as if prefaced by the word "about" even though the term "about" may not expressly appear with the value, amount, or range. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Any patent, publication, internet site, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Unless otherwise defined, all technical and scientific terms used herein have the same meaning as commonly understood by one of ordinary skill in the art.

While the systems, deployment processes and methods have been particularly shown and described with references to embodiments thereof, it will be understood by those skilled in the art that various changes in form and details may be made therein without departing from the scope of the invention encompassed by the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context.

It is also noted that the term "comprising" is intended to be open and permits but does not require the inclusion of additional elements or steps. When the term "comprising" is used herein, the term "consisting of" is thus also encompassed and disclosed. Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. Where the term "about" is used, it is understood to reflect +/−10% of the recited value. In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein.

REFERENCES

[1] H. Khan and J. Paisie, "Global Syngas Overview https://www.slideshare.net/StratasAdvisors/stratas-advisors-global-syngas-overview-bv-dr-habib-khan.

[3] L. F. de Diego, M. Ortiz, J. Adánez, F. García-Labiano, A. Abad, and P. Gayán, "Synthesis gas generation by chemical-looping reforming in a batch fluidized bed reactor using Ni-based oxygen carriers," *Chem. Eng. J.*, 2008, doi: 10.1016/j.cej.2008.06.004.

[4] Y. Cao et al., "Synthesis Gas production with an Adjustable H2/CO ratio through the coal gasification process: effects of coal ranks and methane addition," *Energy & Fuels*, vol. 22, pp. 1720-1730, 2008.

[5] J. Adanez, A. Abad, F. Garcia-Labiano, P. Gayan, and L. F. De Diego, "Progress in chemical-looping combustion and reforming technologies," *Prog. Energy Combust. Sci.*, vol. 38, no. 2, pp. 215-282, 2012, doi: 10.1016/j.pecs.2011.09.001.

[6] M. Tang, L. Xu, and M. Fan, "Progress in oxygen carrier development of methane-based chemical-looping reforming: A review," *Applied Energy*, vol. 151. Elsevier Ltd, pp. 143-156, Aug. 1, 2015, doi: 10.1016/j.apenergy.2015.04.017.

[7] M. Voldsund, K. Jordal, and R. Anantharaman, "Hydrogen Production with $CO_2$ capture," *International J. Hydrog. Energy*, vol. 41, pp. 4669-4992, 2016.

[8] C. Ferguson, T. Crocker, and J. Smyth, "Catalyst for change—Which chemical companies are prepared for the low carbon transition?," 2017.

[9] D. L. Alvarado Virla, "Carbon Supported Metal Carbide Catalysts for the Reduction of Carbon Dioxide," University of Calgary, 2018.

[10] O. Ostrovski and G. Zhang, "Reduction os of Metal Oxides by Methane Containing Gas," Am. Inst. Chem. Eng., vol. 52, no. 1, pp. 300-310, 2006.

[11] G. Zhang and O. Ostrovski, "Reduction of Titania by methane-Hydrogen-Argon Gas Mixture," *Metall. Mater. Trans. B*, vol. 31B, pp. 129-139, 200AD, Accessed: Oct. 11, 2019. [Online]. Available: https://link.springer.com/content/pdf/10.1007%2Fs11663-000-0138-4.pdf.

[12] S. C. Bayham, A. Tong, M. Kathe, and L.-S. Fan, "Chemical looping technology for energy and chemical production," *WIREs Energy Env.*, vol. 5, pp. 216-241, 2016.

[13] J. Adánez, L. F. De Diego, F. García-Labiano, P. Gayán, A. Abad, and J. M. Palacios, "Selection of oxygen carriers for chemical-looping combustion," *Energy and Fuels*, 2004, doi: 10.1021/ef0301452.

[14] S. T. Oyama, *The chemistry of transition metal carbides and nitrides*, First. Surrey: Blackie Academic & Professional, 1996.

[15] Y. Ma, G. Guan, X. Hao, J. Cao, and A. Abudula, "Molybdenum carbide as alternative catalyst for hydrogen production—A review," *Renew. Sustain. Energy Rev.*, vol. 75, pp. 1101-1129, August 2017, doi: 10.1016/J.RSER.2016.11.092.

[16] J. B. Claridge et al., "New Catalysts for the Conversion of Methane to Synthesis Gas: Molybdenum and Tungsten Carbide," *J. Catal.*, vol. 180, no. 1, pp. 85-100, November 1998, doi: 10.1006/jcat.1998.2260.

[17] O. Knacke, O. Kubaschewski, and K. Hesselmann, Thermo-chemical properties of Inorganic Substances, 1991, (2nd ed.). Berlin, N.Y.: Springer, selected pages between p. 68 and 2410.

[18] A. P. E. York, J. B. Claridge, C. Marquez-Alvarez, A. J. Brungs, S. C. Tsang, and M. L. H. Green, "Synthesis of early Transition Metal carbides and their Application for the Reforming of Methane to Synthesis Gas," in 3rd World Congress on Oxidation Catalysis, 1997, pp. 711-720.

[19] D. Giles, S. Som, And S. Aggarwal, "NOx emission characteristics of counterflow syngas diffusion flames with airstream dilution," *Fuel*, vol. 85, no. 12-13, pp. 1729-1742, September 2006, doi: 10.1016/j.fuel.2006.01.027.

[20] National Energy Technology Laboratory, "Range of Syngas Composition Across Different Gasifier Type, and Feedstock Produced by the Gasification of Coal Feedstocks." Accessed: Jul. 22, 2019. [Online]. Available: https://www.netl.doe.gov/sites/default/files/netl-file/Range-of-syngas-Comp.pdf.

[21] J. P. Ciferno and J. J. Marano, "Benchmarking Biomass Gasification Technologies for Fuels, Chemicals and Hydrogen Production," 2002. Accessed: Jul. 22, 2019. [Online]. Available: https://www.netl.doe.gov/sites/default/files/netl-file/BMassGasFinal_0.pdf.

[22] D. C. Lamont and W. J. Thomson, "Dry reforming kinetics over a bulk molybdenum carbide catalyst," *Chem. Eng. Sci.*, vol. 60, no. 13, pp. 3553-3559, July 2005, doi: 10.1016/j.ces.2005.01.021.

[23] C. Fernandes de Oliveira, "Chemical Looping Reforming Using Transition Metal Carbides," University of Calgary, 2020.

[24] D. Hunyadi, I. Sajó, and I. M. Szilágyi, "Structure and thermal decomposition of ammonium metatungstate," Budapest. Accessed: Aug. 19, 2019. [Online]. Available: http://real.mtak.hu/17956/1/2591721 Revised manuscript_Ammonium metatungstate_JTAC.pdf.

[25] G. Collodi and F. Wheeler, "Hydrogen production via steam reforming with CO2 capture," Millan.

[26] H. F. Abbas and W. M. A. Wan Daud, "Hydrogen production by methane decomposition: A review," *International Journal of Hydrogen Energy*, vol. 35, no. 3. pp. 1160-1190, February 2010, doi: 10.1016/j.ijhydene.2009.11.036.

[27] J. M. Giraudon, P. Devassine, J. F. Lamonier, L. Delannoy, L. Leclercq, and G. Leclercq, "Synthesis of tungsten carbides by temperature-programmed reaction with CH4-H2 mixtures. Influence of the CH4 and hydrogen content in the carburizing mixture," *J. Solid State Chem.*, vol. 154, no. 2, pp. 412-426, 2000, doi: 10.1006/jssc.2000.8859.

The invention claimed is:

1. A process for producing syngas including at least $H_2$ and CO, the process comprising:
   a) generating a transition metal carbide by reacting a corresponding transition metal oxide with a fuel to produce a stream of syngas;
   b) combining the transition metal carbide with oxygen to oxidize the transition metal carbide to regenerate the corresponding transition metal oxide and heat, thereby producing a gas output comprising at least one or more oxidized carbon compounds; and
   c) cycling between steps a) and b).

2. The process of claim 1, wherein the oxygen is in a mixture of gases.

3. The process of claim 2, wherein the mixture of gases is air.

4. The process of claim 1, wherein step a) is performed in a first reactor, step b) is performed in a second reactor, the transition metal carbide is transferred to the second reactor prior to step b) and the corresponding transition metal oxide is transferred back to the first reactor before cycling to step a).

5. The process of claim 4, further comprising routing at least a portion of the gas output of the second reactor to mix with the fuel prior to providing the fuel to the first reactor.

6. The process of claim 1, wherein the transition metal carbide and the corresponding transition metal oxide is Mo, W, Mn, or Zr.

7. The process of claim 1, wherein the transition metal of the transition metal carbide and the corresponding transition metal oxide is Mo or W.

8. The process of claim 1, wherein the transition metal of the transition metal carbide and the corresponding transition metal oxide is Mo, and the process is initiated using heptamolybdate tetrahydrate.

9. The process of claim 1, wherein the transition metal of the transition metal carbide and the corresponding transition metal oxide is W and the process is initiated using ammonium metatungstate hydrate.

10. The process of claim 4, wherein the temperature in the first reactor is between about 525° C., to about 1125° C.

11. The process of claim 4, wherein the temperature in the first reactor is between about 525° C. to about 1025° C.

12. The process of claim 1, wherein the fuel comprises $CH_4$, a $C_1$ to $C_4$ hydrocarbon, a fossil fuel mixture, biomass or coal.

13. The process of claim 4, wherein heat generated in the second reactor is used to provide heat to the first reactor.

14. The process of claim 13, wherein excess heat generated in the second reactor not provided to the first reactor is used in a separate process.

15. The process of claim 1, wherein, when the stream of syngas has a ratio of $H_2$/CO exceeding about 3, the syngas is used for production of $H_2$ in a separate process.

16. The process of claim 1, wherein, when the stream of syngas has a ratio of $H_2$/CO below about 3, the syngas is used in a separate Fischer-Tropsch process, methanol production process or dimethyl ether production process.

17. The process of claim 1, wherein $CO_2$ is mixed with the fuel in step a).

18. The process of claim 1, wherein nitrogen is mixed with the fuel in step a) to produce nitrogen compounds for production of fertilizer or ammonia.

19. The process of claim 1, wherein the fuel is greater than about 30% $CH_4$.

20. The process of claim 1, which is performed on fixed bed reactors with switching of gas composition to alternate between a reducing gas mixture and an oxidizing gas mixture with inert gas purging prior to the switching, thereby generating the oxidized carbon compounds without moving the transition metal carbide and the transition metal oxide.

* * * * *